(12) United States Patent
Liu et al.

(10) Patent No.: US 11,712,217 B2
(45) Date of Patent: Aug. 1, 2023

(54) METHODS AND APPARATUSES FOR COLLECTION OF ULTRASOUND IMAGES

(71) Applicant: BFLY OPERATIONS, INC., Guilford, CT (US)

(72) Inventors: Yang Liu, Hoboken, NJ (US); Cristina Shin, San Francisco, CA (US); Nathan Silberman, Brooklyn, NY (US); Audrey Howell, New York, NY (US); Daniel Hertz, New York, NY (US); Swaminathan Sankaranarayanan, Guilford, CT (US)

(73) Assignee: BFLY OPERATIONS, INC., Burlington, MA (US)

( * ) Notice: Subject to any disclaimer, the term of this patent is extended or adjusted under 35 U.S.C. 154(b) by 211 days.

(21) Appl. No.: 16/987,999

(22) Filed: Aug. 7, 2020

(65) Prior Publication Data
US 2021/0038189 A1    Feb. 11, 2021

Related U.S. Application Data
(60) Provisional application No. 62/884,573, filed on Aug. 8, 2019.

(51) Int. Cl.
*A61B 8/08* (2006.01)
*A61B 8/00* (2006.01)

(52) U.S. Cl.
CPC .......... *A61B 8/08* (2013.01); *A61B 8/46* (2013.01); *A61B 8/5223* (2013.01);
(Continued)

(58) Field of Classification Search
CPC ........... A61B 8/08; A61B 8/46; A61B 8/5223; A61B 8/4427; A61B 8/465; A61B 8/483
See application file for complete search history.

(56) References Cited

U.S. PATENT DOCUMENTS

2003/0187353 A1    10/2003  Ng et al.
2006/0173309 A1*    8/2006  Suzuki ................. A61B 8/5238
                                                             600/437
(Continued)

FOREIGN PATENT DOCUMENTS

WO    WO 2017/222970 A1    12/2017

OTHER PUBLICATIONS

International Search Report and Written Opinion dated Nov. 4, 2020 in connection with International Application No. PCT/US2020/045419.

(Continued)

*Primary Examiner* — Katherine L Fernandez
*Assistant Examiner* — Brooke Lyn Klein
(74) *Attorney, Agent, or Firm* — Osha Bergman Watanabe & Burton LLP

(57) ABSTRACT

Aspects of the technology described herein include determining, during ultrasound imaging, that an anatomical region is clipped by a field of view of an ultrasound image, and providing a notification, during the ultrasound imaging, that the anatomical region is clipped by the field of view of the ultrasound image. Aspects of the technology described herein also include determining that an anatomical region is clipped by a field of view of at least one ultrasound image collected during a three-dimensional ultrasound imaging sweep, and providing a notification that the anatomical region is clipped by the field of view of the at least one ultrasound image collected during the three-dimensional ultrasound imaging sweep.

18 Claims, 20 Drawing Sheets

(52) U.S. Cl.
CPC ............. *A61B 8/4427* (2013.01); *A61B 8/465* (2013.01); *A61B 8/483* (2013.01)

(56) References Cited

U.S. PATENT DOCUMENTS

| | | |
|---|---|---|
| 2007/0232882 A1 | 10/2007 | Glossop et al. |
| 2008/0137751 A1 | 6/2008 | Roman |
| 2008/0294045 A1 | 11/2008 | Ellington et al. |
| 2011/0055447 A1 | 3/2011 | Costa |
| 2011/0246521 A1 | 10/2011 | Luo et al. |
| 2015/0116323 A1 | 4/2015 | Buckton et al. |
| 2015/0342560 A1 | 12/2015 | Davey et al. |
| 2016/0367218 A1* | 12/2016 | Kim ..................... A61B 8/4427 |
| 2017/0360397 A1 | 12/2017 | Rothberg et al. |
| 2018/0089530 A1* | 3/2018 | Liu ...................... G06V 10/454 |
| 2019/0142388 A1 | 5/2019 | Gonyeau et al. |
| 2019/0142390 A1* | 5/2019 | Luo .......................... G06N 3/02 600/437 |
| 2019/0196600 A1 | 6/2019 | Rothberg et al. |
| 2019/0282208 A1 | 9/2019 | Silberman et al. |
| 2019/0307428 A1 | 10/2019 | Silberman et al. |
| 2020/0037986 A1 | 2/2020 | Silberman et al. |
| 2020/0037987 A1 | 2/2020 | Silberman et al. |
| 2020/0046322 A1 | 2/2020 | Silberman |
| 2020/0054307 A1 | 2/2020 | Silberman et al. |
| 2020/0214672 A1 | 7/2020 | de Jonge et al. |
| 2020/0214674 A1 | 7/2020 | Gafner et al. |
| 2020/0214679 A1 | 7/2020 | Silberman et al. |
| 2020/0261054 A1 | 8/2020 | Silberman et al. |
| 2021/0007710 A1* | 1/2021 | Douglas ................... A61B 8/54 |
| 2021/0145413 A1* | 5/2021 | Weber ..................... A61B 8/42 |

OTHER PUBLICATIONS

International Search Report and Written Opinion dated Oct. 4, 2020 in connection with International Application No. PCT/US2020/045419.

* cited by examiner

METHODS AND APPARATUSES FOR COLLECTION OF ULTRASOUND IMAGES

CROSS-REFERENCE TO RELATED APPLICATIONS

The present application claims the benefit under 35 U.S.C. § 119(e) of U.S. Application Ser. No. 62/884,573, filed Aug. 8, 2019, and entitled "METHODS AND APPARATUSES FOR COLLECTION OF ULTRASOUND IMAGES," which is hereby incorporated by reference herein in its entirety.

FIELD

Generally, the aspects of the technology described herein relate to collection of ultrasound images.

BACKGROUND

Ultrasound devices may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect of the application, an apparatus, comprises a processing device in operative communication with an ultrasound device, the processing device configured to: determine, during ultrasound imaging, that an anatomical region is clipped by a field of view of an ultrasound image; and provide a notification, during the ultrasound imaging, that the anatomical region is clipped by the field of view of the ultrasound image.

In some embodiments, the processing device is configured, when determining that the anatomical region is clipped by the field of view of the ultrasound image, to determine that a portion of the anatomical region that exceeds a threshold size is within a threshold distance of an edge of the field of view of the ultrasound image. In some embodiments, the processing device is configured, when determining that the anatomical region is clipped by the field of view of the ultrasound image, to use a statistical model. In some embodiments, the processing device is configured, when determining, during the ultrasound imaging, that the anatomical region is clipped by the field of view of the ultrasound image, to determine that the anatomical region is clipped by the field of view of the ultrasound image in a time period between display of a previous ultrasound image and display of a subsequent ultrasound image. In some embodiments, consecutive ultrasound images are displayed with a frame rate approximately equal to or between 15-30 frames/second.

In some embodiments, the processing device is configured, when providing the notification that the anatomical region is clipped by the field of view of the ultrasound image, to display an indicator having an aspect that changes based on whether the anatomical region is clipped by the field of view of the ultrasound image. In some embodiments, the aspect of the indicator comprises a color of the indicator. In some embodiments, the processing device is configured, when displaying the indicator, to display the indicator superimposed on the ultrasound image such that the indicator is located on a specific point of the anatomical region. In some embodiments, the specific point has predetermined mathematical characteristics. In some embodiments, the specific point includes a centroid of the anatomical region.

In some embodiments, the processing device is configured, when providing the notification, to provide the notification in a time period between display of a previous ultrasound image and display of a subsequent ultrasound image. In some embodiments, consecutive ultrasound images are displayed with a frame rate approximately equal to or between 15-30 frames/second.

In some embodiments, the anatomical region comprises a bladder.

According to another aspect of the application, an apparatus comprises a processing device in operative communication with an ultrasound device, the processing device configured to: determine that an anatomical region is clipped by a field of view of at least one ultrasound image collected during a three-dimensional ultrasound imaging sweep; and provide a notification that the anatomical region is clipped by the field of view of the at least one ultrasound image collected during the three-dimensional ultrasound imaging sweep.

In some embodiments, the processing device is configured, when determining that an anatomical region is clipped by the field of view of the at least one ultrasound image collected during the three-dimensional ultrasound imaging sweep, to determine that a portion of the anatomical region that exceeds a threshold size is within a threshold distance of an edge of the field of view of the at least one ultrasound image.

In some embodiments, the three-dimensional ultrasound imaging sweep comprises an elevational sweep.

In some embodiments, the processing device is configured, when providing the notification that the anatomical region is clipped by the field of view of the at least one ultrasound image collected during the three-dimensional ultrasound imaging sweep, to display n indicator that the anatomical region is clipped by the field of view of the at least one ultrasound image collected during the three-dimensional ultrasound imaging sweep. In some embodiments, the indicator comprises text.

In some embodiments, the processing device is further configured to display a measurement of a volume of the anatomical region. In some embodiments, the anatomical region comprises a bladder.

Some aspects include at least one non-transitory computer-readable storage medium storing processor-executable instructions that, when executed by at least one processor, cause the at least one processor to perform the above aspects and embodiments. Some aspects include a method to perform the actions that the processing device is configured to perform.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Figure 1:
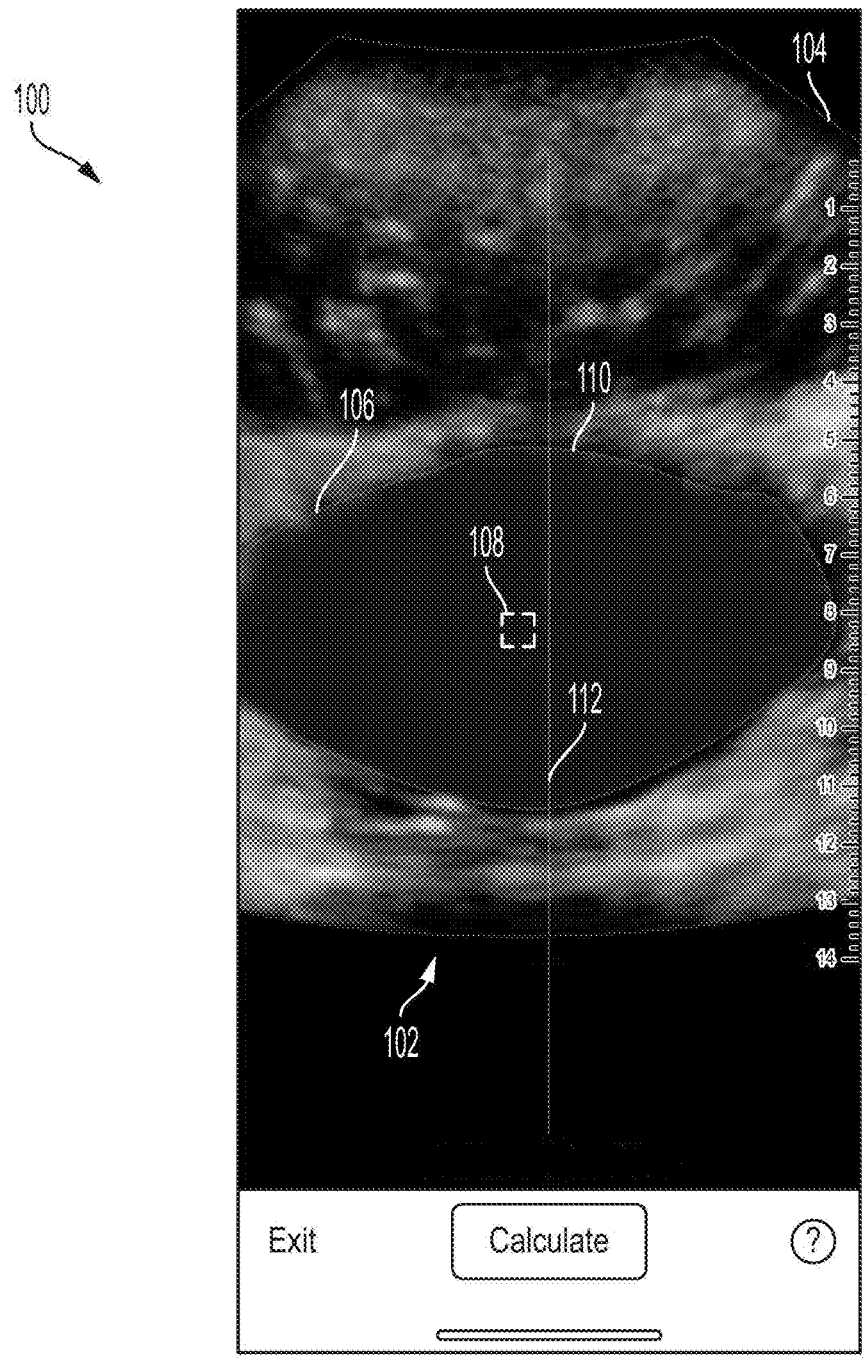
FIG. 1 illustrates an example graphical user interface (GUI), in accordance with certain embodiments described herein.

Some applications of ultrasound imaging include capturing one or more ultrasound images of an anatomical region (e.g., a bladder) with an ultrasound device and performing a clinical measurement based on the ultrasound images. In some embodiments, capturing the ultrasound images may include performing a three-dimensional (3D) ultrasound imaging sweep with the ultrasound device. However, the measurement may be inaccurate if the anatomical region is "clipped" in one or more of ultrasound images used for the measurement. For example, in attempting to measure the volume of a given anatomical structure, if the anatomical structure is clipped in one or more ultrasound images of a three-dimensional imaging sweep on which the measurement is based, then a volume measurement based on the ultrasound images collected during the three-dimensional imaging sweep may be underestimated. An anatomical region may be considered clipped in an ultrasound images if a portion of the anatomical region that exceeds a threshold size is within a threshold distance of an edge of the ultrasound image's field of view (FOV).

In some embodiments, a user may move an ultrasound device over a subject, view ultrasound images collected by the ultrasound device, and position the ultrasound device based on the ultrasound images at a particular location on a subject. The user may initiate a three-dimensional ultrasound imaging sweep from this particular location, which may be, for example, the center of the sweep. The inventors have recognized that when the user is moving the ultrasound device over the subject and viewing ultrasound images collected by the ultrasound device, it may be helpful for a processing device in operative communication with the ultrasound device to determine, during the ultrasound imaging, whether an anatomical region (e.g., a bladder) is clipped in the ultrasound images and provide a notification as to whether the anatomical region is clipped. Based on the notification, the user may choose not to initiate the three-dimensional ultrasound imaging sweep if the anatomical region is clipped in ultrasound images collected from the current location.

The inventors have also recognized that it may be helpful for a processing device to determine that an anatomical region is clipped by a field of view of at least one ultrasound image collected during a three-dimensional ultrasound imaging sweep and provide a notification of such. Thus, a user may understand that a measurement performed based on ultrasound images collected during the three-dimensional ultrasound imaging sweep may be inaccurate.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

FIGS. 1-7 illustrate graphical user interfaces (GUIs) that are displayed by a processing device, in accordance with certain embodiments described herein. The processing device may be, for example, a handheld device such as a mobile phone or tablet, or a laptop. The processing device may be in operative communication with an ultrasound device. The ultrasound device and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link). In some embodiments, the GUIs may be displayed on a touch-sensitive display screen of the processing device. The GUIs may be displayed during ultrasound imaging.

FIG. 1 illustrates an example GUI 100, in accordance with certain embodiments described herein. The GUI 100 includes an ultrasound image 102, an indicator 108, a segmented portion 110, and a vertical line 112. The ultrasound image 102 has a field of view 104 and depicts an anatomical region 106 (in this example, a bladder, but other anatomical regions are possible).

The ultrasound image 102 may be displayed in real-time as it is collected. The field of view (FOV) 104 of the ultrasound image 102 may be those portions of the ultrasound image 102 that include ultrasound data. The FOV 104 may correspond to those locations within a subject from which ultrasound data on which the ultrasound image 102 is based has been collected. In the ultrasound image 102, the FOV 104 is cone-shaped. However, other shapes for the FOV 104 are possible.

The segmented portion 110 may represent the portion of the ultrasound image 102 that has been automatically determined (e.g., by a statistical model) to include the anatomical region 106. The segmented portion 110 may include a marker superimposed on this portion of the ultrasound image 102.

The vertical line 112 may extend vertically through the ultrasound image 102 and may be positioned halfway along the horizontal dimension of the ultrasound image 102.

The indicator 108 may be a marker superimposed on the ultrasound image 102, such that the indicator 108 is located on a specific point of the anatomical region 106. In some embodiments, the specific point may have predetermined mathematical characteristics. In some embodiments, determining the specific point may include using a mathematical formula or algorithm. Examples of the specific point include the centroid of the anatomical region 106 and the point on the anatomical region 106 that is farthest from all the edge points of the anatomical region 106, although other specific points may be used. In some embodiments, a statistical model may be trained to automatically determine the location of a specific point on the anatomical region 106 depicted in the ultrasound image 102. Further description of determining the location for the indicator 108 may be found below.

In FIG. 1, the anatomical region 106 is clipped by the FOV 104 of the ultrasound image 102 at the left edge of the anatomical region 106. The indicator 108 may have a certain color (e.g., red) when the anatomical region 106 is clipped by the FOV 104 of the ultrasound image 102.

Figure 2:
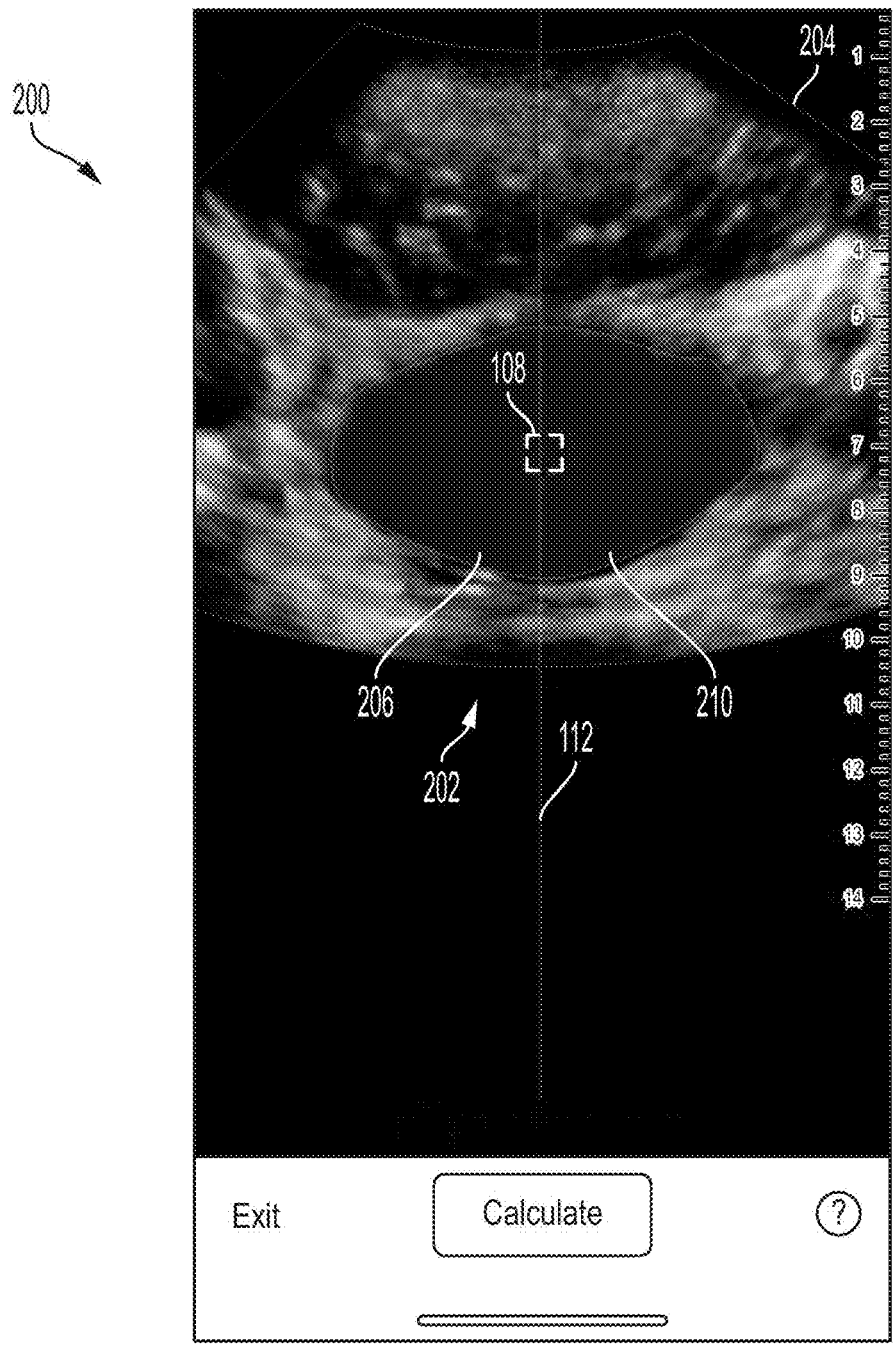
FIG. 2 illustrates another example GUI, in accordance with certain embodiments described herein.

FIG. 2 illustrates an example GUI 200, in accordance with certain embodiments described herein. The GUI 200 includes an ultrasound image 202, a segmented portion 210, and the indicator 108. The ultrasound image 202 has a FOV 204 and depicts an anatomical region 206 (in this example, a bladder, but other anatomical regions are possible). Further description of ultrasound images, FOVs, and segmented portions may be found with reference to the ultrasound image 102, the FOV 104, and the segmented portion 110. In FIG. 2, the anatomical region 206 is not clipped by the FOV 204 of the ultrasound image 202. The indicator 108 may have a certain color (e.g., white) when the anatomical region 206 is not clipped by the FOV 204 of the ultrasound image 202, and that color may be different than the color of the indicator 108 when an anatomical structure is clipped by the FOV of an ultrasound image. In other words, the color of the indicator 108 may change (e.g., from red to white or vice versa) based on whether the anatomical structure is clipped by the FOV of an ultrasound or not. The color of the indicator 108 may thus serve as a notification that an anatomical structure is clipped by the FOV of an ultrasound image. Further description of determining when an anatomical structure is clipped by the FOV of an ultrasound image may be found below. In some embodiments, the color of the indicator 108 may be different depending on whether the anatomical region 106 is centered on the vertical line 112. For example, the indicator 108 may be white when the anatomical region 106 is not clipped but not centered on the vertical line 112 and green when the anatomical region 106 is not clipped and centered on the vertical line 112.

It should be appreciated that the indicator 108 may be displayed on ultrasound images during ultrasound imaging.

In some embodiments, this may mean that the processing device determines whether the anatomical region is clipped by the field of view of an ultrasound image, and displays the indicator 108 with the appropriate color on the ultrasound image, in the time period between display of the previous ultrasound image and display of the subsequent ultrasound image. Consecutive ultrasound images may be displayed with a particular frame rate, where the frame rate may be, for example, approximately equal to or between 15-30 frames/second.

It should be appreciated that other forms for the indicator 108 are possible. For example, the indicator 108 may be a different symbol, such as a circle, an "x," or crosshairs. In some embodiments, other aspects of the indicator 108 may change based on whether an anatomical structure is clipped by the FOV of an ultrasound image or not. For example, the shape or size of the indicator may change.

Figure 3:
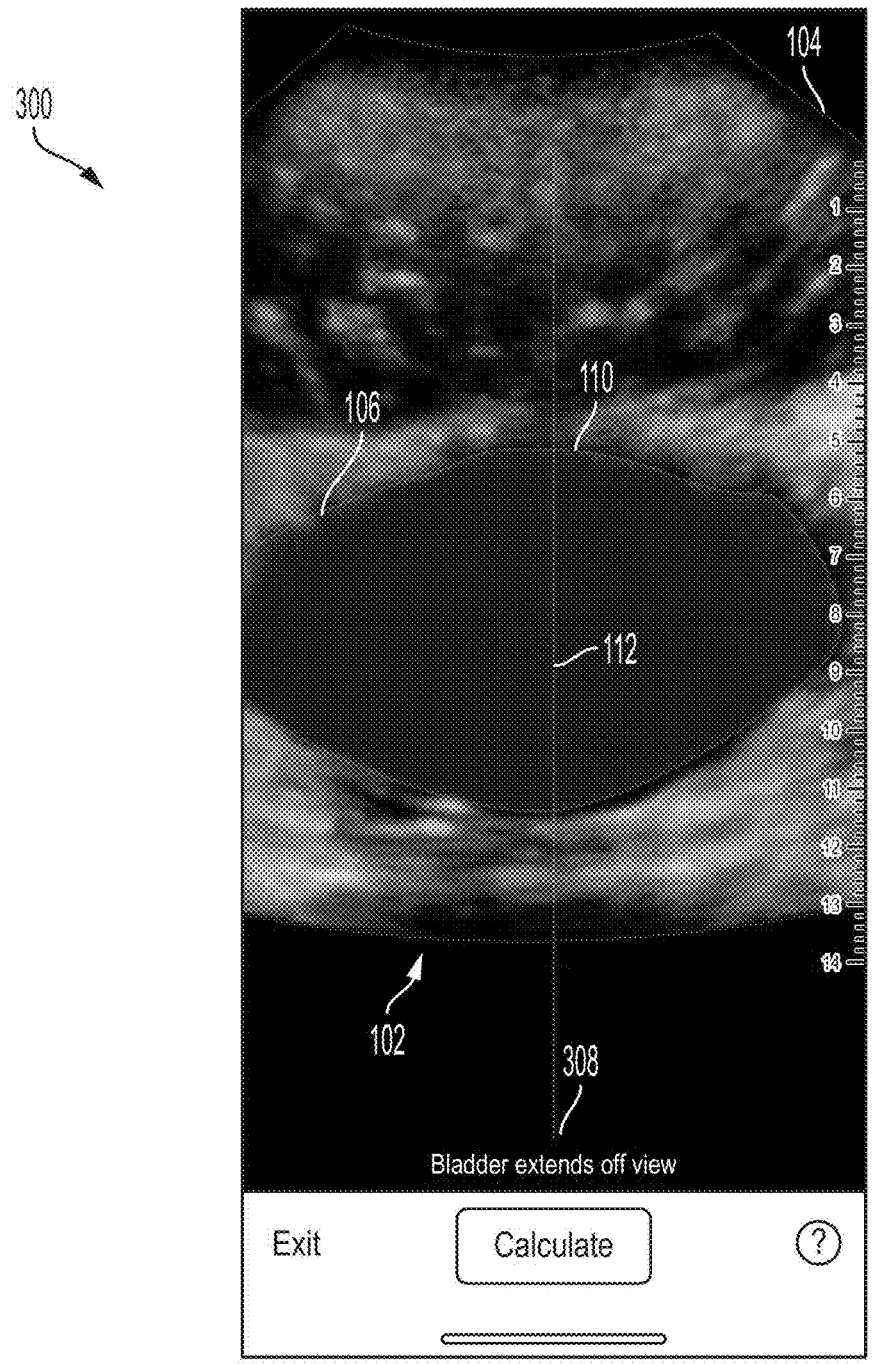
FIG. 3 illustrates another example GUI, in accordance with certain embodiments described herein.

FIG. 3 illustrates an example GUI 300, in accordance with certain embodiments described herein. The GUI 300 in FIG. 3 includes the ultrasound image 102, the segmented portion 110, the vertical line 112, and an indicator 308. As described above, the anatomical region 106 is clipped by the FOV 104 of the ultrasound image 102. The indicator 308, which is text indicating that the anatomical region 106 is clipped by the ultrasound image 102, may be displayed when the anatomical region 106 is clipped by the FOV 104 of the ultrasound image 102.

Figure 4:
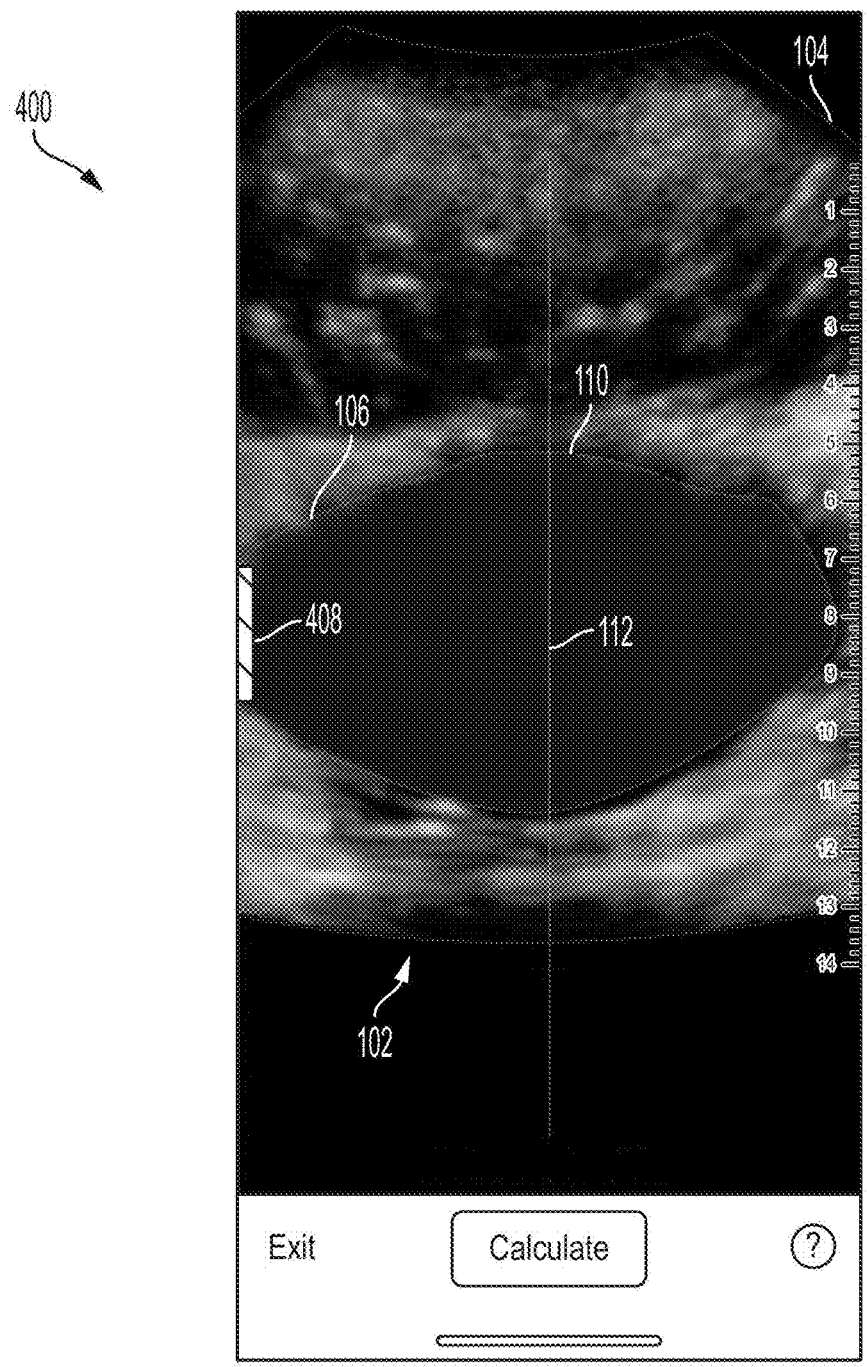
FIG. 4 illustrates another example GUI, in accordance with certain embodiments described herein.

FIG. 4 illustrates an example GUI 400, in accordance with certain embodiments described herein. The GUI 400 in FIG. 4 includes the ultrasound image 102, the segmented portion 110, the vertical line 112, and an indicator 408. As described above, the anatomical region 106 is clipped by the FOV 104 of the ultrasound image 102. The indicator 408 may be a marker superimposed on the portion of the edge of the FOV 104 that is within a threshold distance of the anatomical region 106.

Figure 5:
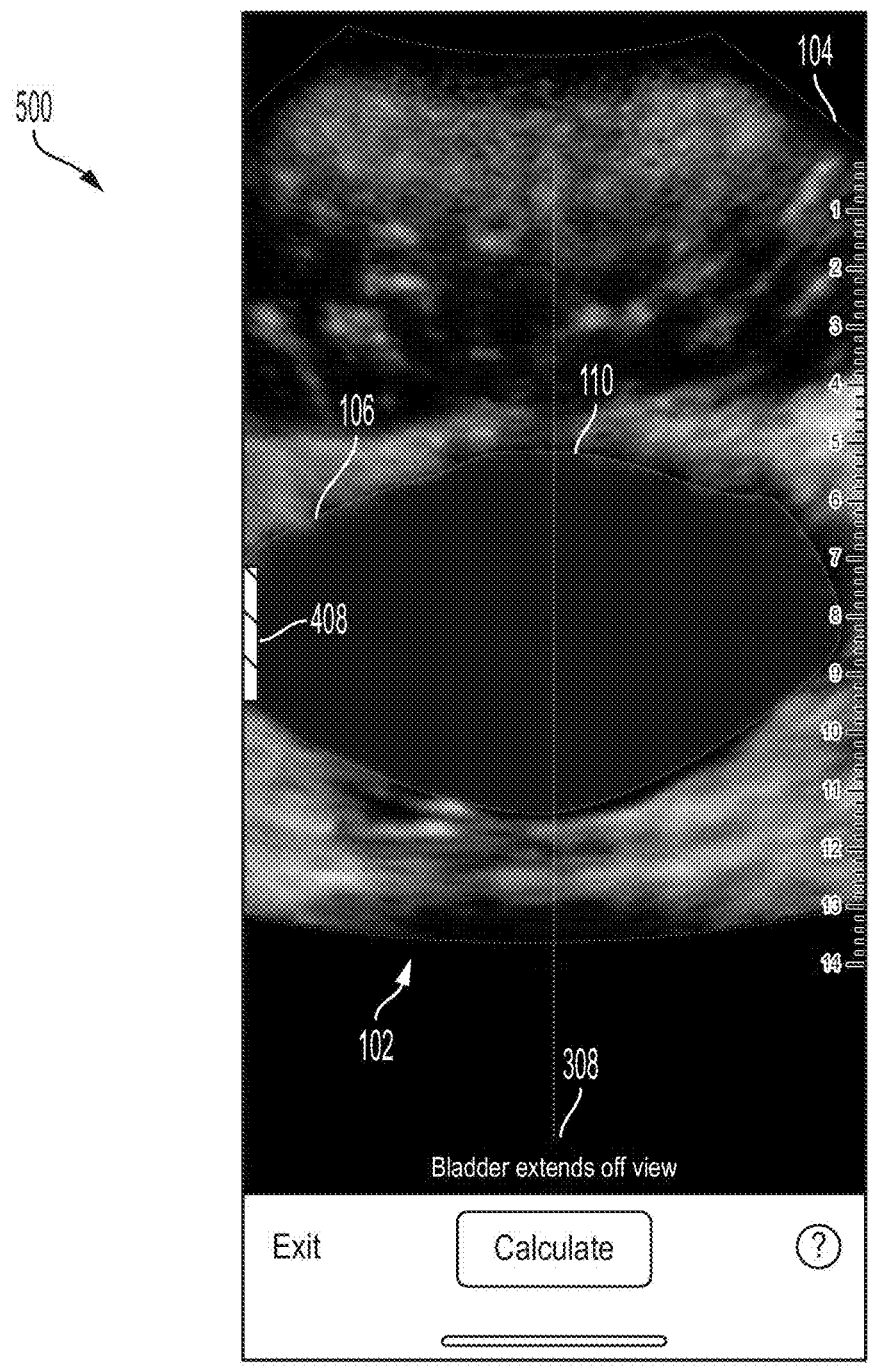
FIG. 5 illustrates another example GUI, in accordance with certain embodiments described herein.

FIG. 5 illustrates an example GUI 500, in accordance with certain embodiments described herein. The GUI 500 in FIG. 5 includes the ultrasound image 102, the segmented portion 110, and both the indicator 308 and the indicator 408. Thus, both the indicator 308 and the indicator 408 may be shown when the anatomical region 106 is clipped by the FOV 104 of the ultrasound image 102.

Figure 6:
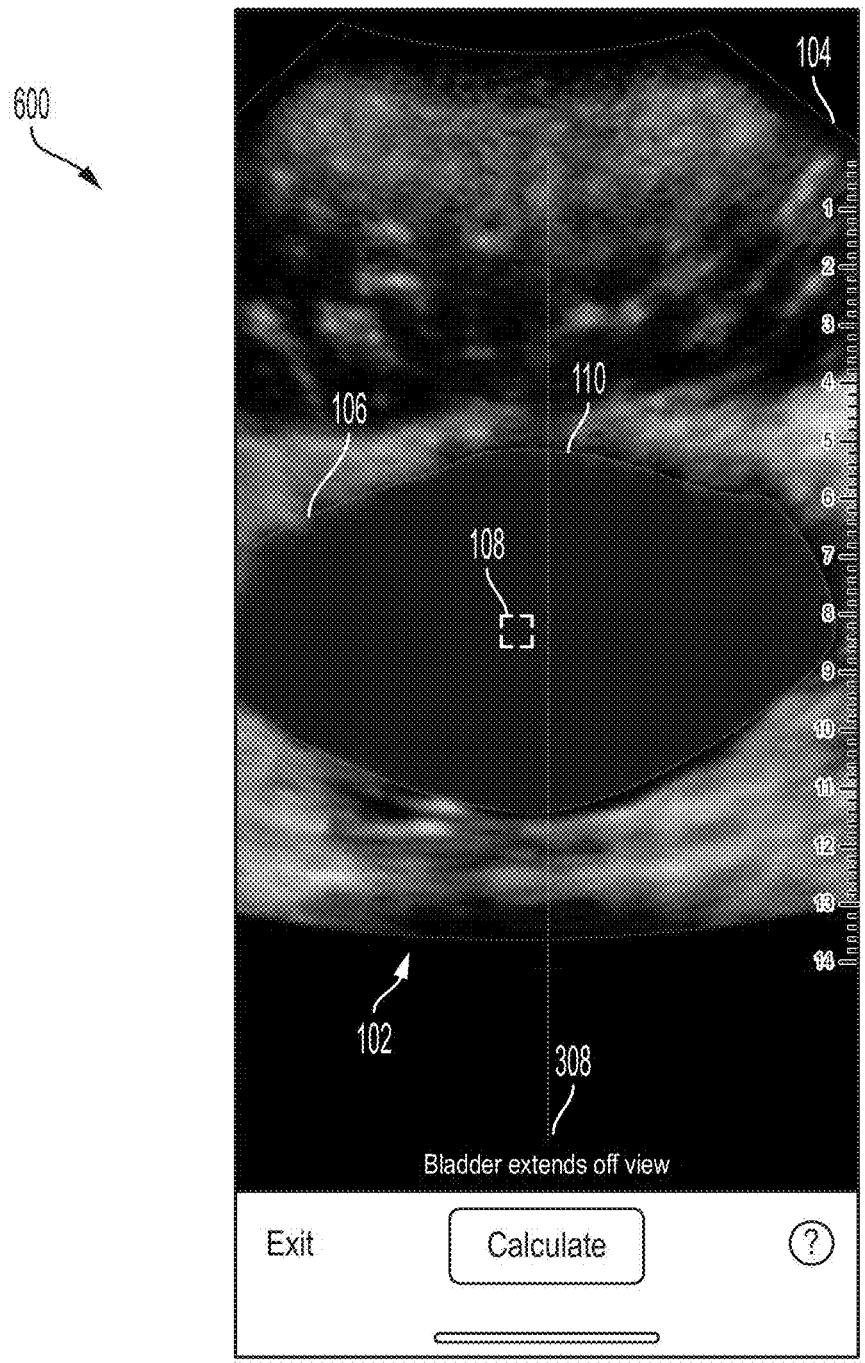
FIG. 6 illustrates another example GUI, in accordance with certain embodiments described herein.

FIG. 6 illustrates an example GUI 600, in accordance with certain embodiments described herein. The GUI 600 in FIG. 6 includes the ultrasound image 102, the segmented portion 110, and both the indicator 108 and the indicator 308. Thus, both the indicator 108 and the indicator 308 may be shown when the anatomical region 106 is clipped by the FOV 104 of the ultrasound image 102. In some embodiments, the indicator 108, the indicator 308, and the indicator 408 may all be displayed together when the anatomical region 106 is clipped by the FOV 104 of the ultrasound image 102.

Figure 7:
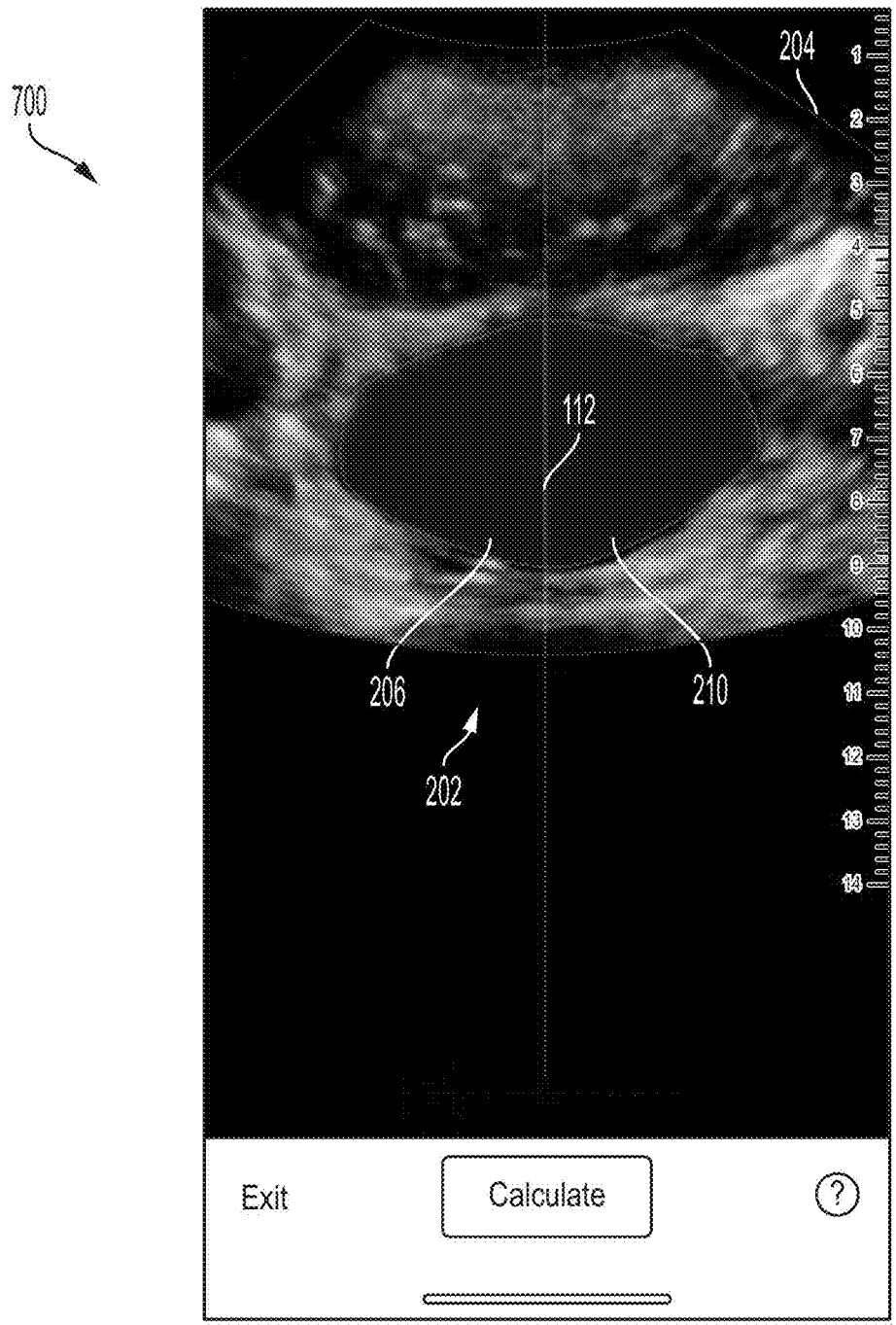
FIG. 7 illustrates another example GUI, in accordance with certain embodiments described herein.

FIG. 7 illustrates an example GUI 700, in accordance with certain embodiments described herein. The GUI 700 includes the ultrasound image 202 and the segmented portion 210. As described above, the anatomical region 206 is not clipped by the FOV 204 of the ultrasound image 202. The indicator 308 and/or the indicator 408 may not be displayed when the anatomical region 206 is not clipped by the FOV 204 of the ultrasound image 202. In other words, the indicator 308 and/or the indicator 408 may be displayed or not based on whether an anatomical structure is clipped by the FOV of an ultrasound image or not. It should be appreciated that the indicator 308 and/or the indicator 408 may be displayed on ultrasound images during ultrasound imaging. In some embodiments, this may mean that the processing device determines whether the anatomical region is clipped by the field of view of an ultrasound image, and causes the indicator 308 and/or the indicator 408 to appear or disappear, in the time period between display of the previous ultrasound image and display of the subsequent ultrasound image. Consecutive ultrasound images may be displayed with a particular frame rate, where the frame rate may be, for example, approximately equal to or between 15-30 frames/second. The presence of the indicator 308 and/or the indicator 408 may thus serve as a notification that an anatomical structure is clipped by the FOV of an ultrasound image. Further description of determining when an anatomical structure is clipped by the FOV of an ultrasound image may be found below.

It should be appreciated that other forms for the indicator 308 are possible. For example, the text of the indicator 308 may be different, or the indicator 308 may be a symbol that appears or disappears based on whether an anatomical structure is clipped by the FOV of an ultrasound image or not. As another example, the indicator 308 may change from one symbol to another (e.g., from an "x" to a checkmark or vice versa) based on whether an anatomical structure is clipped by the FOV of an ultrasound image or not. It should also be appreciated that other forms for the indicator 408 are possible. For example, the indicator 408 may be an arrow pointing to the portion of the edge of the FOV 104 that is within a threshold distance of the anatomical region 106.

As described above, ultrasound images may be displayed in real-time. In some embodiments, an ultrasound image may be considered to be displayed in real-time when a delay between changes in anatomy of a region of a subject imaged by an ultrasound device and changes in the same anatomy displayed by ultrasound images is sufficiently small to be indistinguishable to a human. In some embodiments, an ultrasound image may be considered to be displayed in real-time when the delay between transmission of ultrasound waves from the ultrasound device and display of the ultrasound image generated based on reflections of the transmitted ultrasound waves is less than or equal to 200 milliseconds, less than or equal to 100 milliseconds, and/or less than or equal to 50 milliseconds.

FIGS. 8-14 illustrate graphical user interfaces (GUI) that are displayed by a processing device, in accordance with certain embodiments described herein. The processing device may be, for example, a handheld device such as a mobile phone or tablet, or a laptop. The processing device may be in operative communication with an ultrasound device. The ultrasound device and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link). In some embodiments, the GUIs may be displayed on a touch-sensitive display screen of the processing device. The GUIs may be displayed after a three-dimensional ultrasound imaging sweep that captures multiple ultrasound images. In some embodiments, the three-dimensional ultrasound imaging sweep may be an elevational sweep. In other words, during the three-dimensional ultrasound imaging sweep, the ultrasound device may collect multiple ultrasound images, each ultrasound image collected along a different imaging slice at a different angle along the elevational dimension of the ultrasound device's transducer array. In some embodiments, the sweep may be accomplished through beamforming. In other words, the transducer array of the ultrasound device may remain approximately stationary during the sweep, and beamforming may be used to steer an ultrasound beam to different angles.

Figure 8:
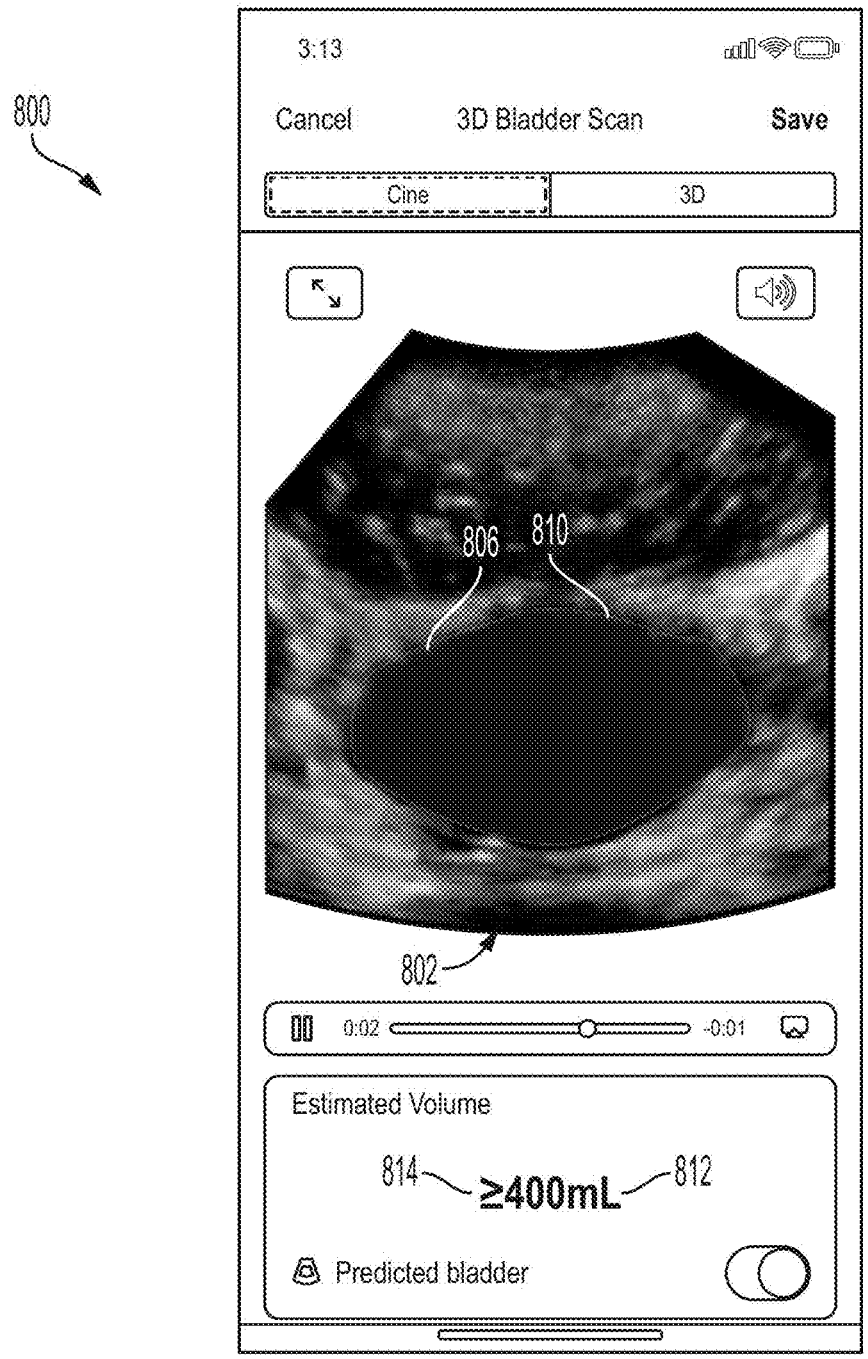
FIG. 8 illustrates another example GUI, in accordance with certain embodiments described herein.

FIG. 8 illustrates an example GUI 800, in accordance with certain embodiments described herein. The GUI 800 includes an ultrasound image 802, a segmented portion 810, a measurement result 812, and an indicator 814. The ultrasound image 802 depicts an anatomical region 806 (in this example, a bladder, although other anatomical regions are possible). Further description of ultrasound images and segmented portions may be found above with reference to the ultrasound image 102 and the segmented portion 110. The measurement result 812 may be a numerical value that is the result of a measurement performed based on one or more ultrasound images captured during a three-dimensional ultrasound imaging sweep, and in particular based on the anatomical region 806 in one or more of the ultrasound images. For example, the measurement result 812 may be the volume of the anatomical structure 806. The indicator 814 may be displayed when, and serve as a notification that, the anatomical region 806 in one or more ultrasound images captured during the three-dimensional ultrasound imaging sweep was clipped (e.g., clipped by an FOV of an ultrasound image). The indicator 814 may indicate that the measurement result 812 may be inaccurate. In particular, the indicator 814 is a greater-than-or-equal-to symbol, which may indicate that the measurement result 812 may underestimate the actual value of the measurement. For example, if the measurement is measuring the volume of anatomical structure, then if the anatomical structure is clipped in one or more ultrasound images of a three-dimensional imaging sweep on which the measurement is based, then measuring the volume based on the ultrasound images collected during the three-dimensional imaging sweep may underestimate the volume. The ultrasound image 802 may be one of the ultrasound images collected during the three-dimensional imaging sweep. In some embodiments, multiple ultrasound images collected during the three-dimensional imaging sweep may be displayed as a cine. In some embodiments, only the ultrasound image(s) in which the anatomical region 806 was clipped may be displayed. In some embodiments, other symbols for the indicator 814 that convey that the measurement value 812 may be inaccurate may be used.

Figure 9:
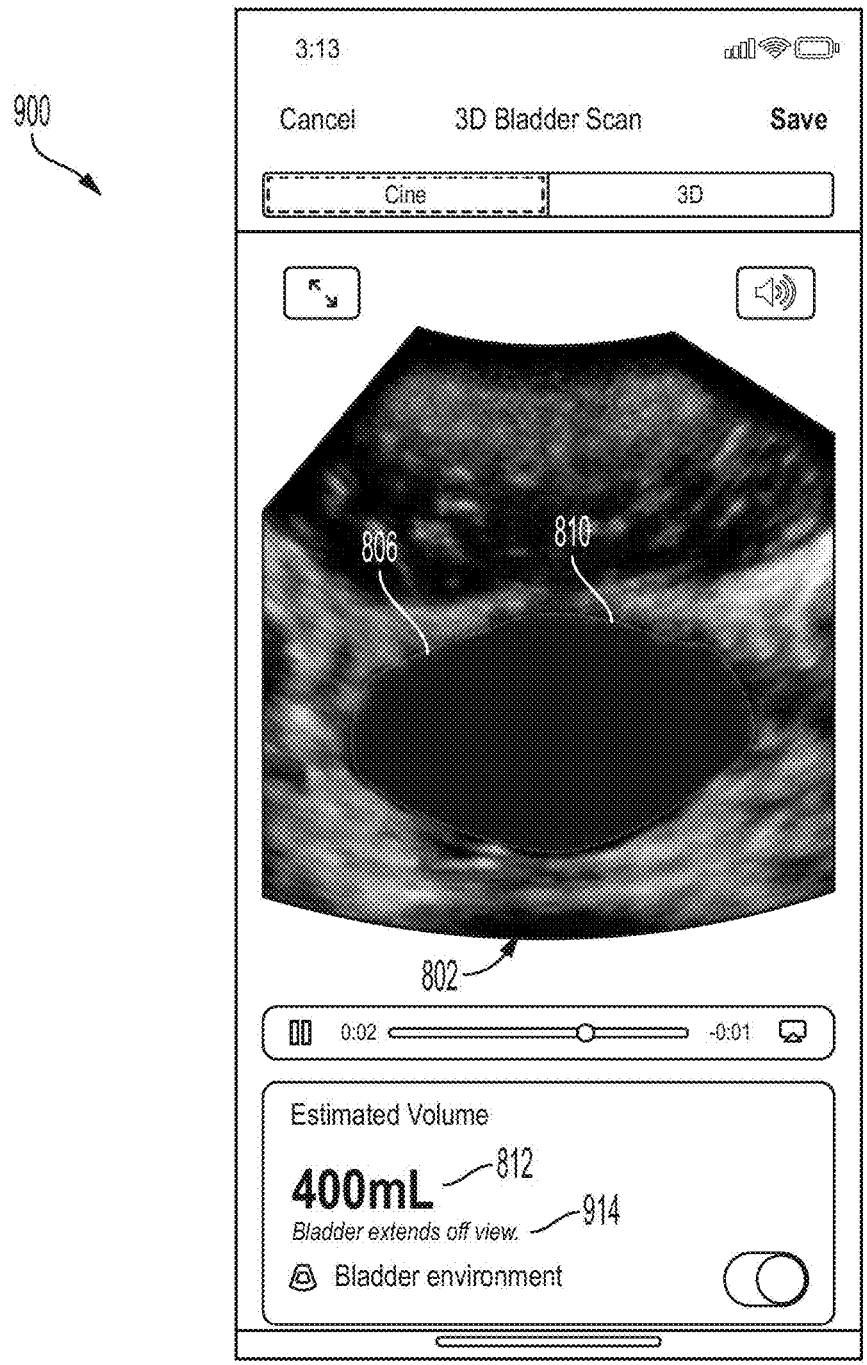
FIG. 9 illustrates another example GUI, in accordance with certain embodiments described herein.

FIG. 9 illustrates an example GUI 900, in accordance with certain embodiments described herein. The GUI 900 includes the measurement result 812, the ultrasound image 802, the segmented portion 810, and an indicator 914. The indicator 914 may be displayed when the anatomical region 806 in one or more ultrasound images captured during the three-dimensional ultrasound imaging sweep was clipped (e.g., clipped by the FOV of the ultrasound images). The indicator 914 includes text indicating that the anatomical region 806 was clipped in one or more of the ultrasound images collected during the three-dimensional ultrasound imaging sweep. In some embodiments, the indicator 914 may include text indicating the measurement result 812 may be inaccurate due to the clipping. In some embodiments, the indicator 914 may include text indicating that the user should try scanning again.

Figure 10:
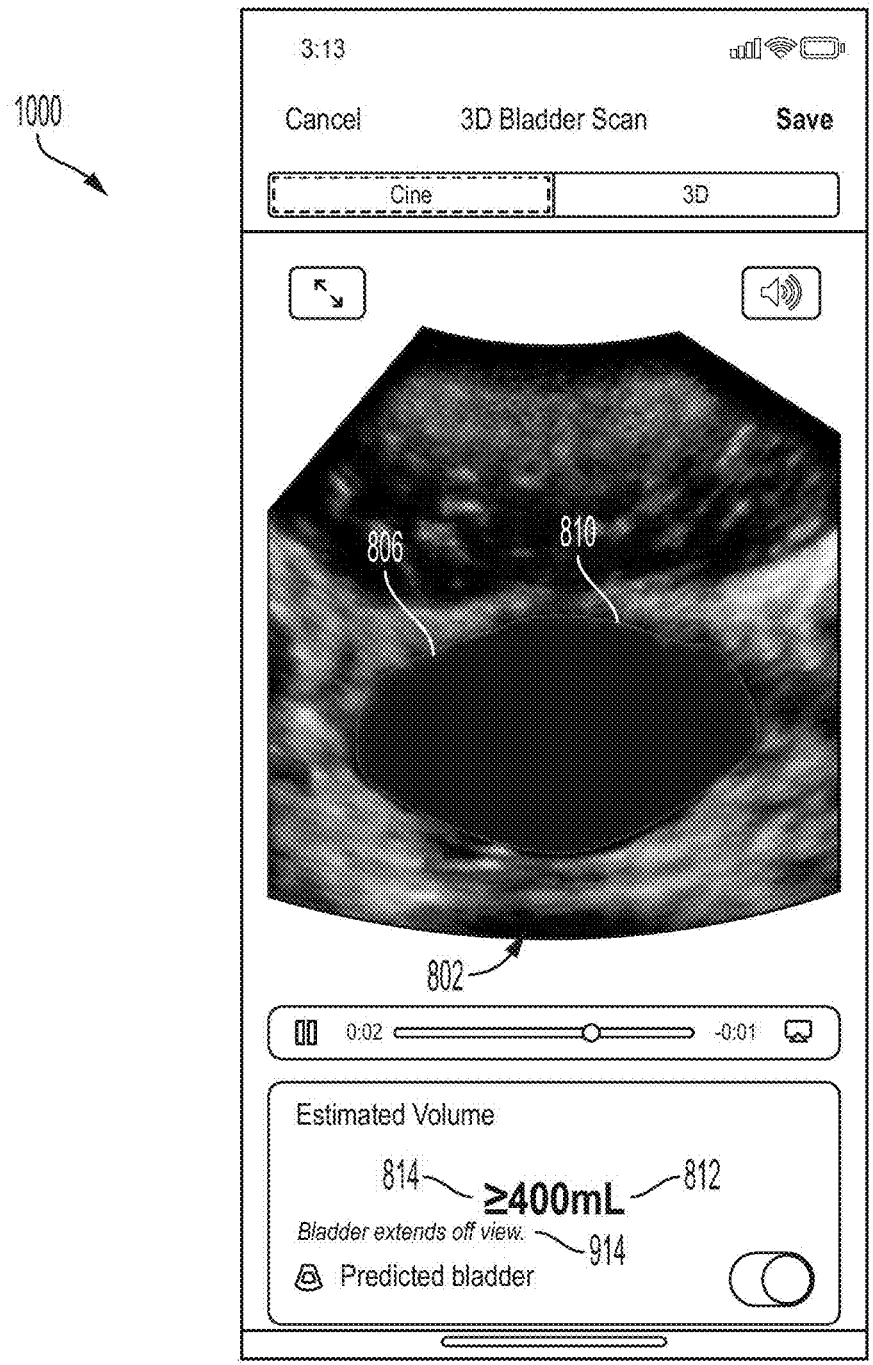
FIG. 10 illustrates another example GUI, in accordance with certain embodiments described herein.

FIG. 10 illustrates an example GUI 1000, in accordance with certain embodiments described herein. The GUI 1000 includes the measurement result 812, the ultrasound image 802, the segmented portion 810, and both the indicator 814 and the indicator 914.

Figure 11:
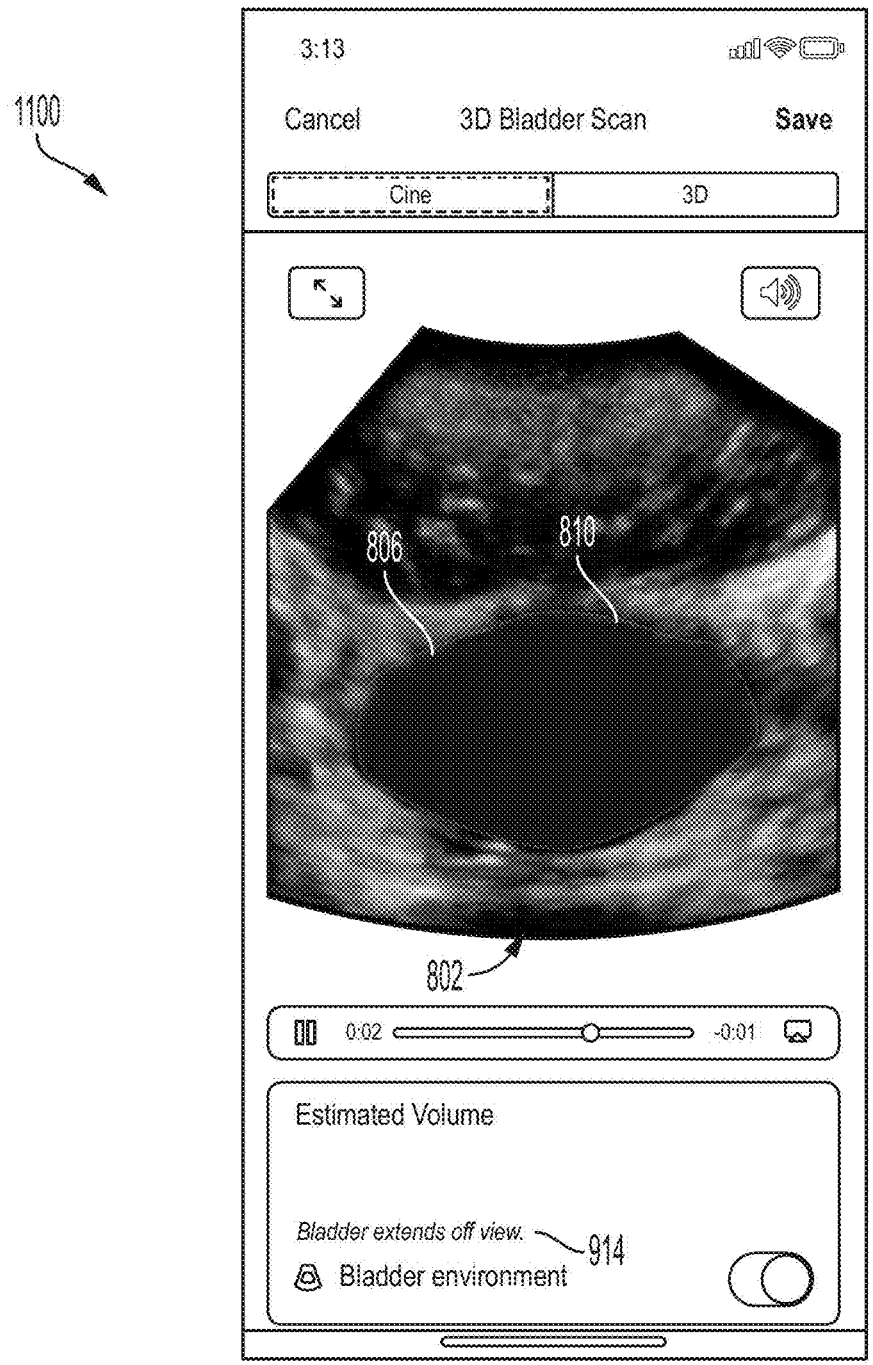
FIG. 11 illustrates another example GUI, in accordance with certain embodiments described herein.

FIG. 11 illustrates an example GUI 1100, in accordance with certain embodiments described herein. The GUI 1100 includes the ultrasound image 802, the segmented portion 810, and the indicator 1114, but lacks the measurement result 812. The indicator 1114 may be displayed when the anatomical region 806 in one or more ultrasound images captured during the three-dimensional ultrasound imaging sweep was clipped (e.g., clipped by the FOV of the ultrasound images). The indicator 1114 includes text indicating that the anatomical region 806 was clipped in one or more of the ultrasound images collected during the three-dimensional ultrasound imaging sweep. In some embodiments, the measurement may not have been performed due to the clipping. In some embodiments, the indicator 914 may include text indicating that the measurement was not performed due to the clipping. In some embodiments, the indicator 914 may include text indicating that the user should try scanning again.

Figure 12:
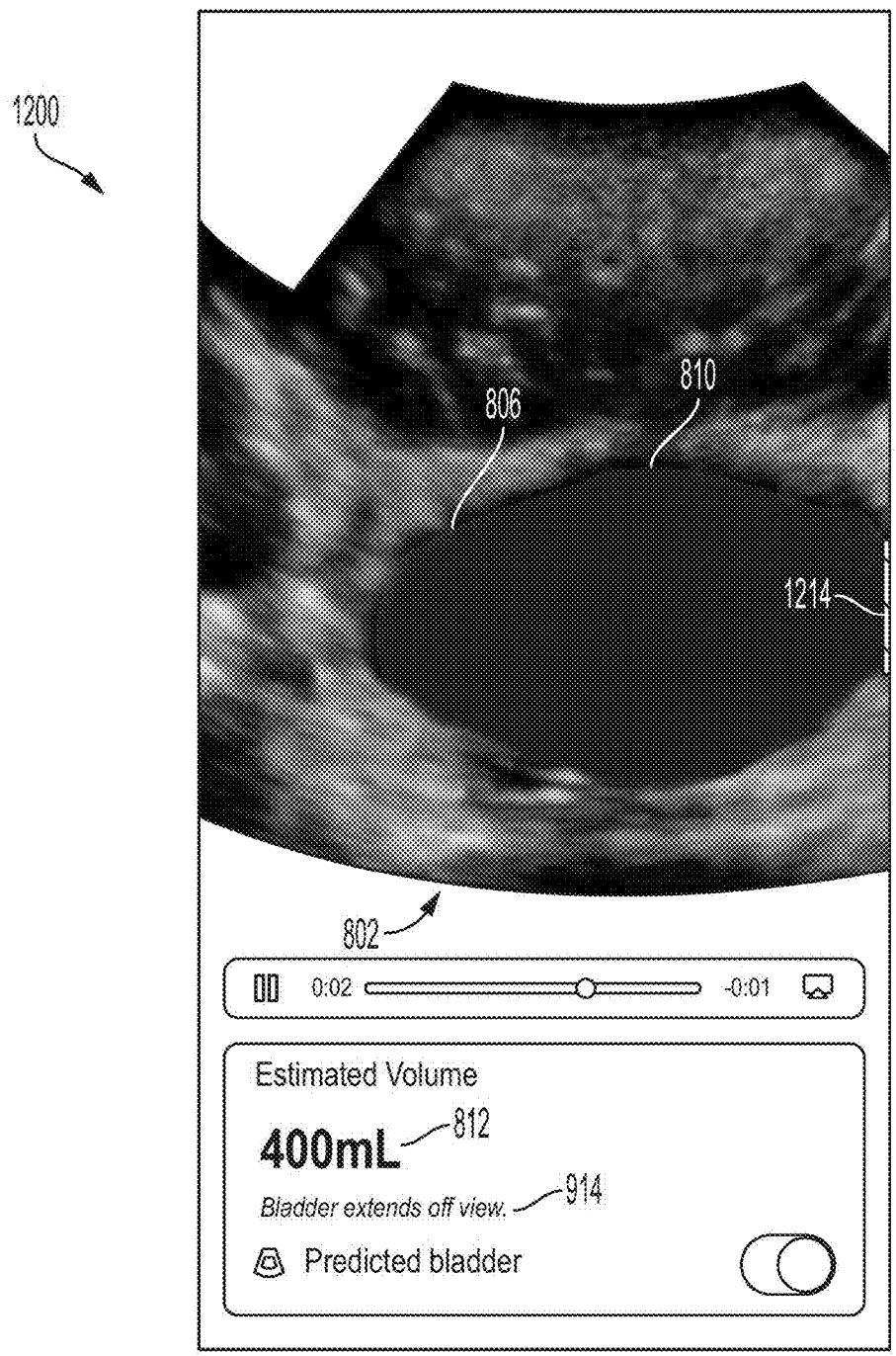
FIG. 12 illustrates another example GUI, in accordance with certain embodiments described herein.

FIG. 12 illustrates an example GUI 1200, in accordance with certain embodiments described herein. The GUI 1200 includes the ultrasound image 802, the segmented portion 810, the measurement result 812, the indicator 914, and an indicator 1214. The indicator 1214 may be a marker superimposed on the portion of the edge of the FOV of the ultrasound image 802 that is within a threshold distance of the anatomical region 806. Further description of the indicator 1214 may be found with reference to the indicator 408. In some embodiments, a combination of two or more of the indicator 814, the indicator 914, and the indicator 1214 may be displayed together.

Figure 13:
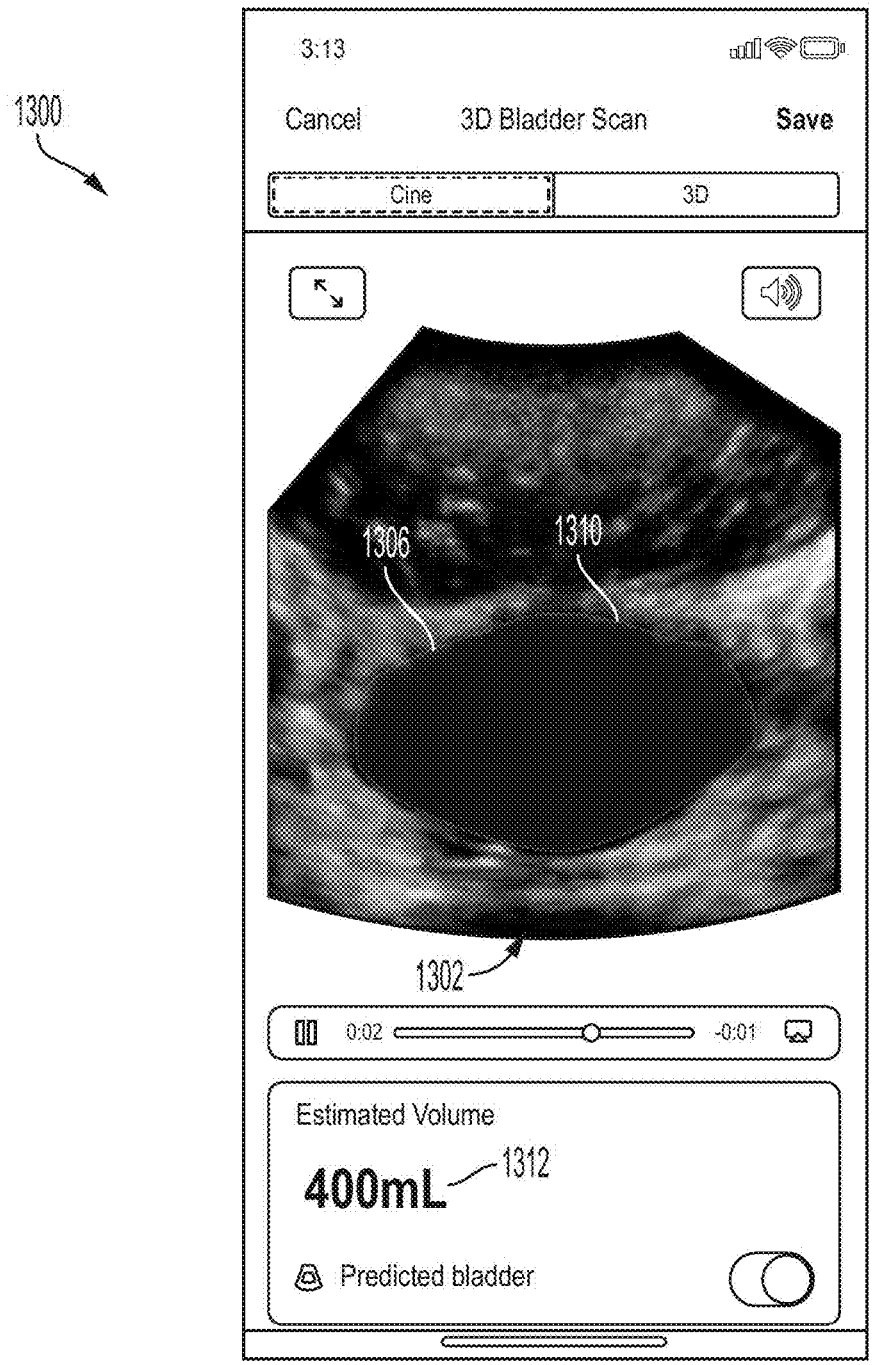
FIG. 13 illustrates another example GUI, in accordance with certain embodiments described herein.

FIG. 13 illustrates an example GUI 1300, in accordance with certain embodiments described herein. The GUI 1300 includes an ultrasound image 1302, a segmented portion 1310, and a measurement result 1312. The ultrasound image depicts an anatomical region 1306. Further description of ultrasound images, segmented portions, measurement results, and anatomical regions may be found with reference to the ultrasound image 802, the segmented portion 810, the measurement result 812, and the anatomical region 806. The GUI 1300 may be displayed when the anatomical region 1306 was not clipped in any ultrasound images captured during the three-dimensional ultrasound imaging sweep. The GUI 1300 lacks any indicators indicating that an anatomical region 1306 in one or more ultrasound images captured during the three-dimensional ultrasound imaging sweep was clipped.

Figure 14:
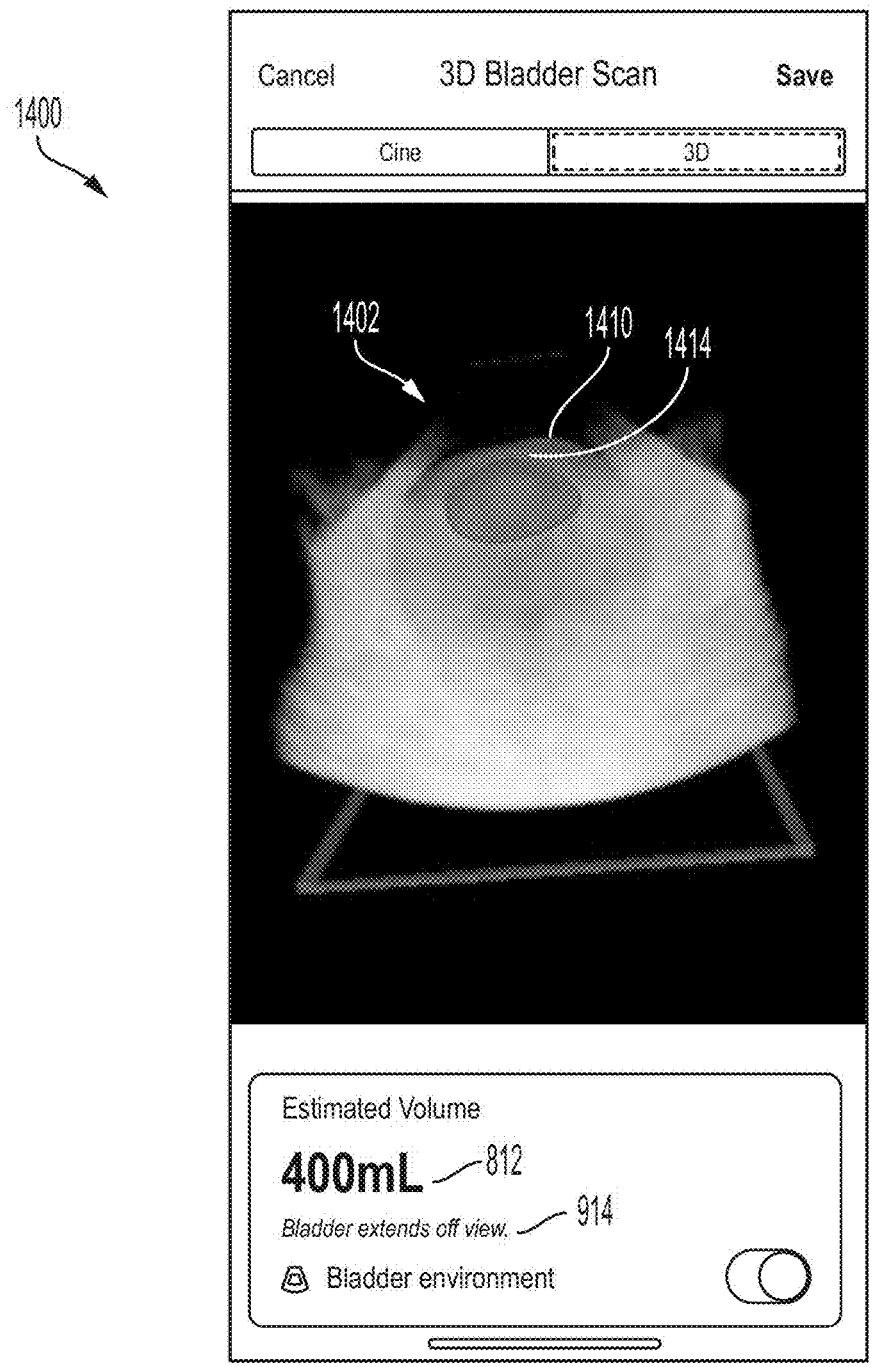
FIG. 14 illustrates another example GUI, in accordance with certain embodiments described herein.

FIG. 14 illustrates an example GUI 1400, in accordance with certain embodiments described herein. The GUI 1400 includes a three-dimensional visualization 1402, the measurement result 812, the indicator 914, and an indicator 1414. The three-dimensional visualization 1402 may be based on one or more ultrasound images from the three-dimensional ultrasound imaging sweep. The three-dimensional visualization 1402 includes a three-dimensional segmented portion 1410 that may represent the portion of the three-dimensional visualization 1402 that has been automatically determined (e.g., by a statistical model) to include the anatomical region. The indicator 1414 may be a marker superimposed on the portion of the edge of the FOV of the three-dimensional visualization 1402 that is within a threshold distance of the anatomical region 806. In other words, the indicator 1414 may be a three-dimensional visualization of one or more indicators (like the indicator 1214) from the one or more ultrasound images generated from the three-dimensional visualization. The indicator 1414 may be displayed when, and serve as a notification that, the anatomical region in one or more ultrasound images captured during the three-dimensional ultrasound imaging sweep was clipped (e.g., clipped by an FOV of an ultrasound image). In some embodiments, a combination of two or more of the indicator 814, the indicator 914, and the indicator 1414 may be displayed together.

Figure 15:
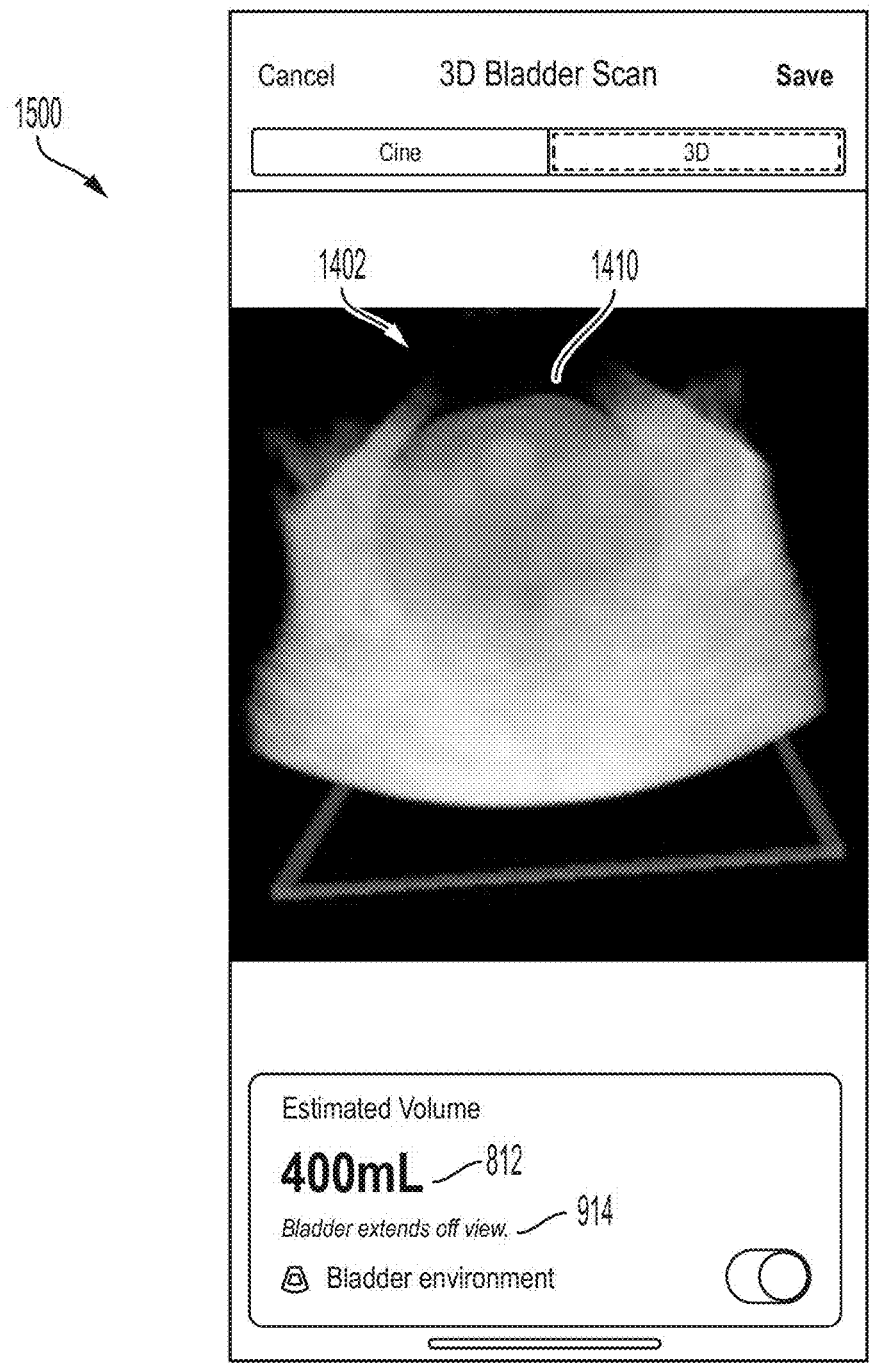
FIG. 15 illustrates another example GUI, in accordance with certain embodiments described herein.

FIG. 15 illustrates an example GUI 1500, in accordance with certain embodiments described herein. The GUI 1500 includes the three-dimensional visualization 1402, the measurement result 812, and the indicator 914.

Figure 16:
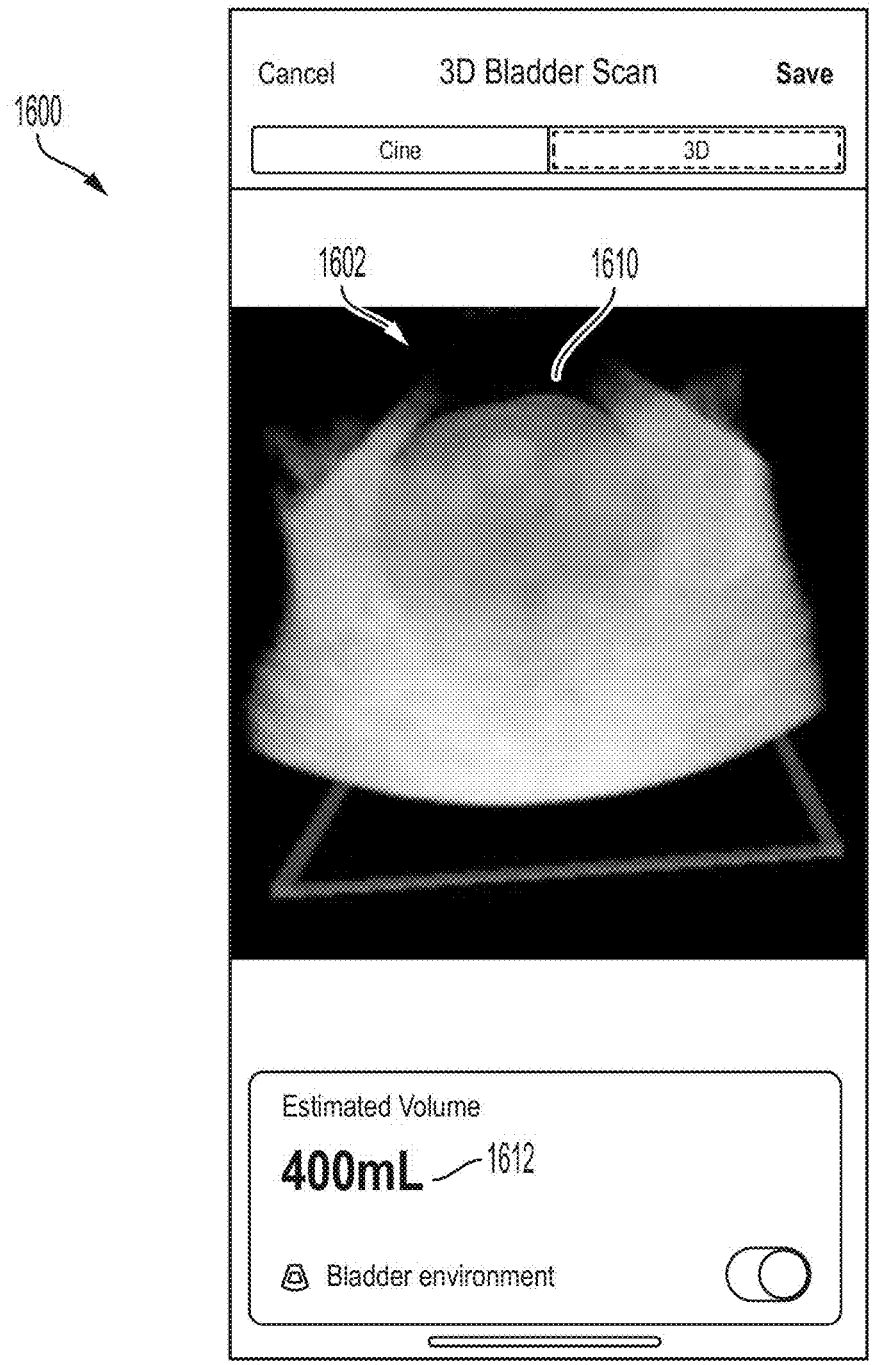
FIG. 16 illustrates another example GUI, in accordance with certain embodiments described herein.

FIG. 16 illustrates an example GUI 1600, in accordance with certain embodiments described herein. The GUI 1600 includes a three-dimensional visualization 1602, a three-dimensional segmented portion 1610, and a measurement result 1612. Further description of three-dimensional visualizations, three-dimensional segmented portions, and measurement results may be found with reference to the three-dimensional visualization 1402, the three-dimensional segmented portion 1410, and the measurement result 812. The GUI 1600 may be displayed when the anatomical region was not clipped in any ultrasound images captured during the three-dimensional ultrasound imaging sweep. The GUI 1600 lacks any indicators indicating that an anatomical region in one or more ultrasound images captured during the three-dimensional ultrasound imaging sweep was clipped.

Figure 17:
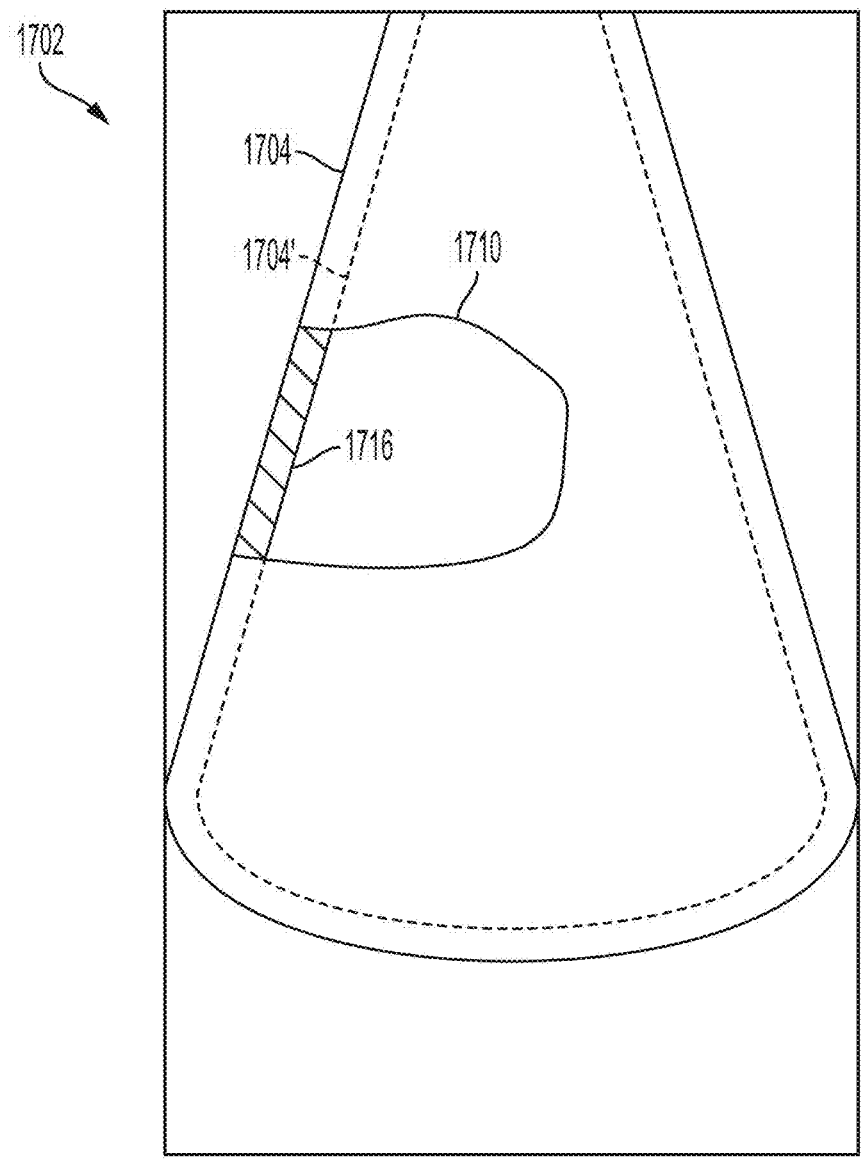
FIG. 17 illustrates a method for determining whether an anatomical region is clipped by a field of view (FOV) in an ultrasound image, in accordance with certain embodiments described herein.

FIG. 17 illustrates a method for determining whether an anatomical region is clipped by a FOV in an ultrasound image, in accordance with certain embodiments described herein. FIG. 17 illustrates a schematic of an ultrasound image 1702. The ultrasound image 1702 includes a FOV 1704. The ultrasound image 1702 also includes an anatomical region (not illustrated in FIG. 17). FIG. 17 illustrates a segmented portion 1710 that represents the portion of the ultrasound image 1702 that has been automatically determined (e.g., by a statistical model) to include the anatomical region. In some embodiments, a statistical model may be trained to determine the location of the anatomical region as depicted in ultrasound images. In some embodiments, the statistical model may be trained on multiple pairs of input and output training data sets as a segmentation model. Each set of input training data may be an ultrasound image depicting the anatomical region. Each set of output training data may be a segmentation mask that is an array of values equal in size to the input training data ultrasound image, and pixels corresponding to locations including the anatomical region in the ultrasound image are manually set to 1 and other pixels are set to 0. Based on this training data, the statistical model may learn to output, based on an inputted ultrasound image (e.g., the ultrasound image 1702), a segmentation mask where each pixel has a value representing the probability that the pixel corresponds to a location within the anatomical region in the ultrasound image (values closer to 1) or outside the anatomical structure (values closer to 0). The processing device may select all pixels in the segmentation mask that have a value greater than a threshold value (e.g., 0.5) as being within the anatomical region. The segmented portion 1710 may be those pixels. The statistical model may be, for example, a convolutional neural network, a fully connected neural network, a recurrent neural network (e.g., a long short-term memory (LSTM) recurrent neural network), a random forest, a support vector machine, a linear classifier, and/or any other statistical model, and may use deep learning techniques to generate the segmented portion 1710.

FIG. 17 further illustrates a modified FOV 1704'. The modified FOV 1704' may be generated based on the FOV 1704. For example, the modified FOV 1704' may be generated by offsetting the edges of the FOV 1704 toward the center of the ultrasound image 1702. The number of pixels in a region 1716 of the segmented portion 1710 that are between the FOV 1704 and the modified FOV 1704' may be determined. If this number of pixels exceeds a threshold number of pixels, the anatomical region in the ultrasound image 1702 may be considered to be clipped in the ultrasound image 1702. A processing device may determine the segmented portion 1710, determine the modified FOV 1704' (or retrieve a pre-determined modified FOV 1704'), determine the number of pixels in the region 1716 of the segmented portion 1710 that are between the FOV 1704 and the modified FOV 1704', and determine if the number of pixels exceeds the threshold number of pixels. The processing device may be, for example, a handheld device such as a mobile phone or tablet, or a laptop. The processing device may be in operative communication with an ultrasound device. The ultrasound device and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link).

As described above, in some embodiments an indicator (e.g., the indicator 408) may be superimposed on the portion of the edge of the FOV that is within a threshold distance of the anatomical structure. In some embodiments, such an indicator may be superimposed on the region 1716 of the segmented portion 1710 that is between the FOV 1704 and the modified FOV 1704'.

Figure 18:
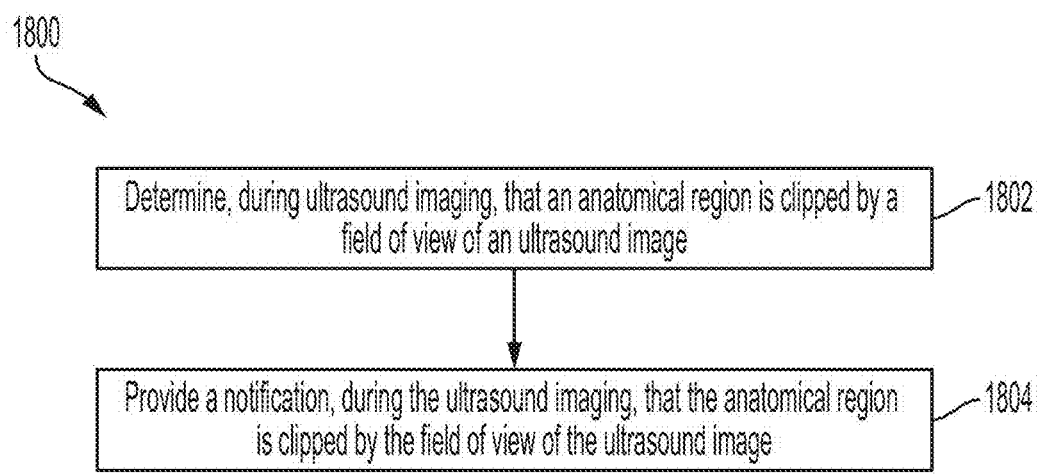
FIG. 18 illustrates an example process for collection of ultrasound images, in accordance with certain embodiments described herein.

FIG. 18 illustrates an example process 1800 for collection of ultrasound images, in accordance with certain embodiments described herein. The process 1800 is performed by a processing device. The processing device may be, for example, a handheld device such as a mobile phone or tablet, or a laptop. The processing device may be in operative communication with an ultrasound device. The ultrasound device and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link). In some embodiments, the process 1800 may be performed by the ultrasound device itself.

In act 1802, the processing device determines, during ultrasound imaging, that an anatomical region is clipped by a field of view of an ultrasound image. The processing device may perform this determination automatically. The field of view (FOV) of the ultrasound image may be those portions of the ultrasound image that include ultrasound data. The FOV may correspond to those locations within a subject from which ultrasound data on which the ultrasound image is based has been collected. In some embodiments, determining that the anatomical region is clipped by the FOV of the ultrasound image may include automatically determining a segmented portion that represents the portion of the ultrasound image includes the anatomical region. In some embodiments, a statistical model may be trained to determine the location of the anatomical region as depicted in ultrasound images. In some embodiments, the statistical model may be trained on multiple pairs of input and output training data sets as a segmentation model. Each set of input training data may be an ultrasound image depicting an anatomical region. Each set of output training data may be a segmentation mask that is an array of values equal in size to the input training data ultrasound image, and pixels corresponding to locations including the anatomical region in the ultrasound image are manually set to 1 and other pixels are set to 0. Based on this training data, the statistical model may learn to output, based on an inputted ultrasound image, a segmentation mask where each pixel has a value representing the probability that the pixel corresponds to a location within the anatomical region in the ultrasound image (values closer to 1) or outside the anatomical structure (values closer to 0). The processing device may select all pixels in the segmentation mask that have a value greater than a threshold value (e.g., 0.5) as being within the anatomical region. The segmented portion may be those pixels. The statistical model may be, for example, a convolutional neural network, a fully connected neural network, a recurrent neural network (e.g., a long short-term memory (LSTM) recurrent neural network), a random forest, a support vector machine, a linear classifier, and/or any other statistical model, and may use deep learning techniques to generate the segmented portion.

In some embodiments, the processing device may further generate a modified FOV (or retrieve a pre-determined modified FOV) which may be generated based on the FOV of the ultrasound image. For example, the modified FOV may be generated by offsetting the edges of the FOV of the ultrasound image toward the center of the ultrasound image. The processing device may determine the number of pixels in the segmented portion that are between the FOV of the ultrasound image and the modified FOV. If this number of pixels exceeds a threshold number of pixels, the processing device may determine that the anatomical region is clipped by the field of view of the ultrasound image. Further description of determining whether an anatomical region is clipped by the field of view of an ultrasound image may be found with reference to FIG. 17.

The processing device determines that the anatomical region is clipped by the field of view of the ultrasound image during the ultrasound imaging. In some embodiments, this may mean that the processing device determines that the anatomical region is clipped by the field of view of an ultrasound image in the time period between display of the previous ultrasound image and display of the subsequent ultrasound image. Consecutive ultrasound images may be displayed with a particular frame rate, where the frame rate may be, for example, approximately equal to or between 15-30 frames/second. The process 1800 proceeds from act 1802 to act 1804.

In act 1804, the processing device provides a notification, during the ultrasound imaging, that the anatomical region is clipped by the field of view of the ultrasound image. The processing device may provide the notification automatically, based on the determination in act 1802. In some embodiments, the color of an indicator may serve as a notification that the anatomical structure is clipped by the FOV of an ultrasound image. The indicator may be a marker superimposed on the ultrasound image, such that the indicator is located on a specific point of the anatomical region. In some embodiments, the specific point may have predetermined mathematical characteristics. In some embodiments, determining the specific point may include using a mathematical formula or algorithm. Examples of the specific point include the centroid of the anatomical region and the point on the anatomical region that is farthest from all the edge points of the anatomical region, although other specific points may be used. In some embodiments, a statistical model may be trained to automatically determine the location of a specific point on the anatomical structure depicted in the ultrasound image. Further description of determining the location for the indicator may be found above. The indicator may have a certain color (e.g., red) when the anatomical structure is clipped by the FOV of the ultrasound image and another color (e.g., white) when the anatomical structure is not clipped by the FOV of the ultrasound image.

In some embodiments, the presence of an indicator may serve as a notification that an anatomical structure is clipped by the FOV of the ultrasound image. In some embodiments, the indicator may be text stating that the anatomical structure is clipped by the ultrasound image. In some embodiments, the indicator may be a symbol (e.g., an "x"). In some embodiments, the indicator may be a marker that is superimposed on the portion of the edge of the FOV that is within a threshold distance of the anatomical structure. As described above, the processing device provides the notification that the anatomical region is clipped by the field of view of the ultrasound image during the ultrasound imaging. In some embodiments, this may mean that the processing device determines whether the anatomical region is clipped by the field of view of an ultrasound image, and displays the indicator with the appropriate color on the ultrasound image, in the time period between display of the previous ultrasound image and display of the subsequent ultrasound image. In some embodiments, this may mean that the processing device determines whether the anatomical region is clipped by the field of view of an ultrasound image, and causes an indicator to appear or disappear, in the time period between display of the previous ultrasound image and display of the subsequent ultrasound image. Consecutive ultrasound images may be displayed with a particular frame rate, where the frame rate may be, for example, approximately equal to or between 15-30 frames/second. In some embodiments, multiple indicators may be outputted.

Figure 19:
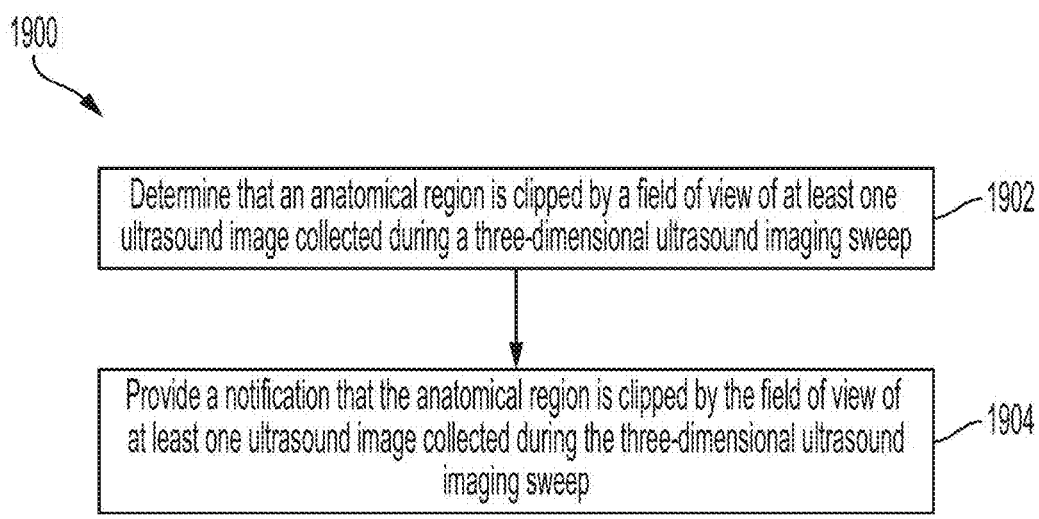
FIG. 19 illustrates another example process for collection of ultrasound images, in accordance with certain embodiments described herein.

FIG. 19 illustrates an example process 1900 for collection of ultrasound images, in accordance with certain embodiments described herein. The process 1900 is performed by a processing device. The processing device may be, for example, a handheld device such as a mobile phone or tablet, or a laptop. The processing device may be in operative communication with an ultrasound device. The ultrasound device and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link).

In act 1902, the processing device determines that an anatomical region is clipped by a field of view of at least one ultrasound image collected during a three-dimensional ultrasound imaging sweep. The processing device my perform the determination automatically. In some embodiments, the three-dimensional ultrasound imaging sweep may be an elevational sweep. In other words, during the three-dimensional ultrasound imaging sweep, the ultrasound device may collect multiple ultrasound images, each ultrasound image collected along a different imaging slice at a different angle along the elevational dimension of the ultrasound device's transducer array. Further description of determining whether an anatomical region is clipped by a field of view of at least one ultrasound image may be found with reference to act 1802. In some embodiments, the processing device may determine whether the anatomical region is clipped by the field of view of ultrasound images as the ultrasound images are collected. In some embodiments, this may mean that the processing device determines that the anatomical region is clipped by the field of view of an ultrasound image in the time period between collection of the previous ultrasound image and collection of the subsequent ultrasound image. Consecutive ultrasound images may be collected during the three-dimensional ultrasound imaging sweep with a particular frame rate, where the frame rate may be, for example, approximately equal to or between 4-15 frames/second. In some embodiments, the processing device may determine whether the anatomical region is clipped by the field of view of any of the ultrasound images after the ultrasound images are collected. The process 1900 proceeds from act 1902 to act 1904.

In act 1904, the processing device provides a notification that the anatomical region is clipped by the field of view of at least one ultrasound image collected during the three-dimensional ultrasound imaging sweep. The processing device may provide the notification automatically, based on the determination in act 1902. In some embodiments, the processing device may output a measurement result, which may include a numerical value that is the result of a measurement performed based on one or more ultrasound images captured during the three-dimensional ultrasound imaging sweep. For example, the measurement result may be the volume of an anatomical structure such as a bladder. The processing device may further output an indicator that is a notification that an anatomical region in one or more ultrasound images captured during the three-dimensional ultrasound imaging sweep was clipped. In some embodiments, the indicator may be a greater-than-or-equal-to symbol, which may indicate that the measurement result may underestimate the actual value of the measurement. For example, if the measurement is measuring the volume of anatomical structure, then if the anatomical structure is clipped in one or more ultrasound images of a three-dimensional imaging sweep on which the measurement is based, then measuring the volume based on the ultrasound images collected during the three-dimensional imaging sweep may underestimate the volume. In some embodiments, the notification may include an indicator that includes text indicating that the anatomical region was clipped in one or more of the ultrasound images. In such embodiments, the measurement result may be displayed or not displayed. For example, in some embodiments, the measurement may not be performed if the anatomical region was clipped in one or more ultrasound images. In such embodiments, the indicator may include text indicating that the measurement was not performed due to the clipping. In embodiments in which the measurement is performed, the indicator may include text indicating that the measurement result may be inaccurate due to the clipping. In some embodiments, multiple indicators may be displayed.

The above description has described determining that an anatomical region is clipped by a field of view of an ultrasound image and providing a notification that an anatomical region is clipped by the field of view of an ultrasound image. It should be appreciated that this may mean determining that a particular anatomical region (or regions) of interest is clipped by a field of view of an ultrasound image and providing a notification that the particular anatomical region (or regions) of interest is clipped by the field of view of an ultrasound image. In other words, it may not be determined whether any anatomical region is clipped, and a notification may not be provided whenever any anatomical region is clipped. For example, if an ultrasound system is configured for calculating the volume of a bladder, the ultrasound system may only determine whether the bladder is clipped by a field of view of an ultrasound image and may only provide a notification that the bladder is clipped by the field of view of an ultrasound image.

As described above, certain embodiments include an indicator (e.g., the indicator 108) that may be superimposed on an ultrasound image, such that the indicator is located on a specific point of the anatomical region. In some embodiments, the specific point may have predetermined mathematical characteristics. In some embodiments, determining the specific point may include using a mathematical formula or algorithm. Examples of the specific point include the centroid of the anatomical region and the point on the anatomical region that is farthest from all the edge points of the anatomical region, although other specific points may be used. In some embodiments, a statistical model may be trained to automatically determine the location of a specific point on the anatomical structure depicted in the ultrasound image. The statistical model may be stored on the processing device or stored on another electronic device (e.g., a server) and accessed by the processing device.

For the example where the specific point is the centroid of the anatomical structure, in some embodiments, the statistical model may be trained on multiple pairs of input and output training data sets as a segmentation model. Each set of input training data may be an ultrasound image depicting an anatomical structure. Each set of output training data may be a segmentation mask that is an array of values equal in size to the input training data ultrasound image, and pixels corresponding to locations within the anatomical structure in the ultrasound image are manually set to 1 and other pixels are set to 0. Based on this training data, the statistical model may learn to output, based on an inputted ultrasound image, a segmentation mask where each pixel has a value representing the probability that the pixel corresponds to a location within the anatomical structure in the ultrasound image (values closer to 1) or outside the anatomical structure (values closer to 0). The processing device may select all pixels in the segmentation mask that have a value greater than a threshold value (e.g., 0.5) as being within the anatomical structure. To determine the location of the centroid of the anatomical structure depicted in the ultrasound image, the processing device may calculate the arithmetic mean of all the locations of pixels that were determined to be within the anatomical structure. For example, the processing device may calculate the arithmetic mean of the horizontal locations of all pixels within the anatomical structure and the arithmetic mean of the vertical locations of all pixels within the anatomical structure. The processing device may determine the location of the centroid of the anatomical structure to be the pixel having a horizontal position that is at the arithmetic mean of all pixels within the anatomical structure and having a vertical position that is at the arithmetic mean of all pixels within the anatomical structure.

In some embodiments, the statistical model may be trained on multiple pairs of input and output training data sets as a keypoint localization model. Each set of input training data may be an ultrasound image depicting an anatomical structure. Each set of output training data may be an array of values that is the same size as the input training data ultrasound image, where the pixel corresponding to the centroid of the anatomical structure in the ultrasound image is manually set to a value of 1 and every other pixel has a value of 0. Based on this training data, the statistical model may learn to output, based on an inputted ultrasound image, an array of values that is the same size as the inputted image, where each pixel in the array consists of a probability that that pixel is where the centroid of an anatomical structure depicted in the ultrasound image is located. The processing device may select the pixel having the highest probability as the location of the specific point on the anatomical structure in the ultrasound image.

In some embodiments, the statistical model may be trained on multiple pairs of input and output training data sets to use regression. Each set of input training data may be an ultrasound image depicting an anatomical structure. Each set of output training data set may be the pixel location of the centroid of the anatomical structure in the input training data ultrasound image. Based on this training data, the statistical model may learn to output, based on an inputted ultrasound image, the horizontal and vertical pixel coordinates of the centroid of an anatomical structure depicted in the ultrasound device.

For the example where the specific point is the point on the anatomical structure that is farthest from all the edge points of the anatomical structure, in some embodiments, the statistical model may be trained on multiple pairs of input and output training data sets as a segmentation model. Each set of input training data may be an ultrasound image depicting an anatomical structure. Each set of output training data may be a segmentation mask that is an array of values equal in size to the input training data ultrasound image, and pixels corresponding to locations on the boundary of the anatomical structure in the ultrasound image are manually set to 1 and other pixels are set to 0. Based on this training data, the statistical model may learn to output, based on an inputted ultrasound image, a segmentation mask where each pixel has a value representing the probability that the pixel corresponds to a boundary of the anatomical structure in the ultrasound image (values closer to 1) or does not correspond to a boundary of the anatomical structure (values closer to 0). The processing device may select all pixels in the segmentation mask that have a value greater than a threshold value (e.g., 0.5) as being on the boundary of the anatomical structure. To determine the location of the point on the anatomical structure that is farthest from all the edge points of the anatomical structure depicted in the ultrasound image, the processing device may calculate, for every pixel inside the boundary, the sum of the distances of that pixel to every pixel on the boundary. The processing device may then select the pixel having the greater sum of distances as the location of the specific point on the anatomical structure in the ultrasound image.

In some embodiments, the statistical model may be trained on multiple pairs of input and output training data sets as a keypoint localization model. Each set of input training data may be an ultrasound image depicting an anatomical structure. Each set of output training data may be an array of values that is the same size as the input training data ultrasound image, where the pixel corresponding to the point on the anatomical structure that is farthest from all the edge points of the anatomical structure in the ultrasound image is manually set to a value of 1 and every other pixel has a value of 0. Based on this training data, the statistical model may learn to output, based on an inputted ultrasound image, an array of values that is the same size as the inputted image, where each pixel in the array consists of a probability that that pixel is where the point on the anatomical structure that is farthest from all the edge points of the anatomical structure in the ultrasound image is located. The processing device may select the pixel having the highest probability as the location of the specific point on the anatomical structure in the ultrasound image.

In some embodiments, the statistical model may be trained on multiple pairs of input and output training data sets to use regression. Each set of input training data may be an ultrasound image depicting an anatomical structure. Each set of output training data set may be the pixel location of the point on the anatomical structure that is farthest from all the edge points of the anatomical structure. Based on this training data, the statistical model may learn to output, based on an inputted ultrasound image, the horizontal and vertical pixel coordinates of the point on the anatomical structure that is farthest from all the edge points of the anatomical structure. The indicator of the location of the specific point on the anatomical structure may include a symbol (e.g., a circle, an "x", a crosshairs, etc.) and may be located at the location of the specific point on the anatomical structure. For example, one of the pixels of the symbol may be at the location of the specific point on the anatomical structure in the ultrasound image (or is the pixel closest to this location). The symbol may be centered at the location of the specific point, or the center of the symbol may be at the pixel which is closest to this location. In some embodiments, the indicator of the location of the specific point on the anatomical structure may not be located at the location of the specific point, but at a location that is based on the location of the specific point (e.g., a certain number of pixels away from the specific point in a particular direction). In some embodiments, only one indicator (namely, the indicator of the location of the specific point on the anatomical structure) may be displayed on the anatomical structure, and no other indicators of locations on the anatomical structure may be displayed. While the above description has described the indicator as being positioned at a specific point on an anatomical region, it should be understood that this may mean that the indicator is being positioned at a specific point on a segmented portion of an ultrasound image corresponding to the anatomical region.

Figure 20:
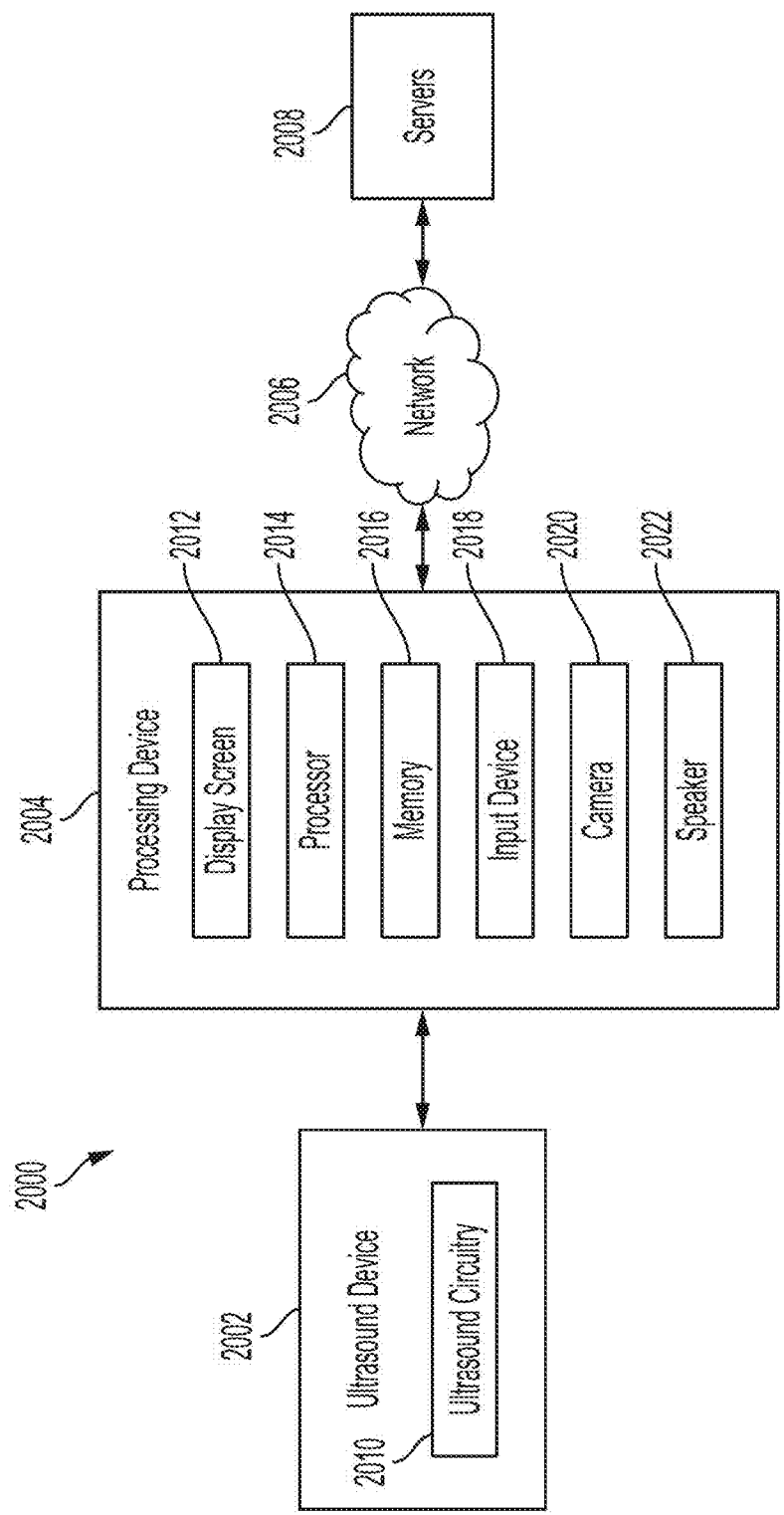
FIG. 20 illustrates a schematic block diagram of an example ultrasound system upon which various aspects of the technology described herein may be practiced.

FIG. 20 illustrates a schematic block diagram of an example ultrasound system 2000 upon which various aspects of the technology described herein may be practiced. The ultrasound system 2000 includes an ultrasound device 2002, a processing device 2004, a network 2006, and one or more servers 2008. The processing device 2004 may be any of the processing devices described herein. The ultrasound device 2002 may be any of the ultrasound devices described herein.

The ultrasound device 2002 includes ultrasound circuitry 2010. The processing device 2004 includes a camera 2020, a display screen 2012, a processor 2014, a memory 2016, an input device 2018, and a speaker 2022. The processing device 2004 is in wired (e.g., through a lightning connector or a mini-USB connector) and/or wireless communication (e.g., using BLUETOOTH, ZIGBEE, and/or WiFi wireless protocols) with the ultrasound device 2002. The processing device 2004 is in wireless communication with the one or more servers 2008 over the network 2006.

The ultrasound device 2002 may be configured to generate ultrasound data that may be employed to generate an ultrasound image. The ultrasound device 2002 may be constructed in any of a variety of ways. In some embodiments, the ultrasound device 2002 includes a transmitter that transmits a signal to a transmit beamformer which in turn drives transducer elements within a transducer array to emit pulsed ultrasonic signals into a structure, such as a patient. The pulsed ultrasonic signals may be back-scattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data. The ultrasound circuitry 2010 may be configured to generate the ultrasound data. The ultrasound circuitry 2010 may include one or more ultrasonic transducers monolithically integrated onto a single semiconductor die. The ultrasonic transducers may include, for example, one or more capacitive micromachined ultrasonic transducers (CMUTs), one or more CMOS (complementary metal-oxide-semiconductor) ultrasonic transducers (CUTs), one or more piezoelectric micromachined ultrasonic transducers (PMUTs), and/or one or more other suitable ultrasonic transducer cells. In some embodiments, the ultrasonic transducers may be formed on the same chip as other electronic components in the ultrasound circuitry 2010 (e.g., transmit circuitry, receive circuitry, control circuitry, power management circuitry, and processing circuitry) to form a monolithic ultrasound device. The ultrasound device 2002 may transmit ultrasound data and/or ultrasound images to the processing device 2004 over a wired (e.g., through a lightning connector or a mini-USB connector) and/or wireless (e.g., using BLUETOOTH, ZIGBEE, and/or WiFi wireless protocols) communication link.

Referring now to the processing device 2004, the processor 2014 may include specially-programmed and/or special-purpose hardware such as an application-specific integrated circuit (ASIC). For example, the processor 2014 may include one or more graphics processing units (GPUs) and/or one or more tensor processing units (TPUs). TPUs may be ASICs specifically designed for machine learning (e.g., deep learning). The TPUs may be employed, for example, to accelerate the inference phase of a neural network. The processing device 2004 may be configured to process the ultrasound data received from the ultrasound device 2002 to generate ultrasound images for display on the display screen 2012. The processing may be performed by, for example, the processor 2014. The processor 2014 may also be adapted to control the acquisition of ultrasound data with the ultrasound device 2002. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data may be sequentially displayed. Additionally, or alternatively, the ultrasound data may be stored temporarily in a buffer during a scanning session and processed in less than real-time.

The processing device 2004 may be configured to perform certain of the processes (e.g., the processes 1800-1900) described herein using the processor 2014 (e.g., one or more computer hardware processors) and one or more articles of manufacture that include non-transitory computer-readable storage media such as the memory 2016. The processor 2014 may control writing data to and reading data from the memory 2016 in any suitable manner. To perform certain of the processes described herein, the processor 2014 may execute one or more processor-executable instructions stored in one or more non-transitory computer-readable storage media (e.g., the memory 2016), which may serve as non-transitory computer-readable storage media storing processor-executable instructions for execution by the processor 2014. The camera 2020 may be configured to detect light (e.g., visible light) to form an image. The camera 2020 may be on the same face of the processing device 2004 as the display screen 2012. The display screen 2012 may be configured to display images and/or videos, and may be, for example, a liquid crystal display (LCD), a plasma display, and/or an organic light emitting diode (OLED) display on the processing device 2004. The input device 2018 may include one or more devices capable of receiving input from a user and transmitting the input to the processor 2014. For example, the input device 2018 may include a keyboard, a mouse, a microphone, touch-enabled sensors on the display screen 2012, and/or a microphone. The display screen 2012, the input device 2018, the camera 2020, and the speaker 2022 may be communicatively coupled to the processor 2014 and/or under the control of the processor 2014.

It should be appreciated that the processing device 2004 may be implemented in any of a variety of ways. For example, the processing device 2004 may be implemented as a handheld device such as a mobile smartphone or a tablet. Thereby, a user of the ultrasound device 2002 may be able to operate the ultrasound device 2002 with one hand and hold the processing device 2004 with another hand. In other examples, the processing device 2004 may be implemented as a portable device that is not a handheld device, such as a laptop. In yet other examples, the processing device 2004 may be implemented as a stationary device such as a desktop computer. The processing device 2004 may be connected to the network 2006 over a wired connection (e.g., via an Ethernet cable) and/or a wireless connection (e.g., over a WiFi network). The processing device 2004 may thereby communicate with (e.g., transmit data to or receive data from) the one or more servers 2008 over the network 2006. For example, a party may provide from the server 2008 to the processing device 2004 processor-executable instructions for storing in one or more non-transitory computer-readable storage media (e.g., the memory 2016) which, when executed, may cause the processing device 2004 to perform certain of the processes (e.g., the processes 1800-1900) described herein.

For further description of ultrasound devices and systems, see U.S. patent application Ser. No. 15/415,434 titled "UNIVERSAL ULTRASOUND DEVICE AND RELATED APPARATUS AND METHODS," filed on Jan. 25, 2017 and published as U.S. Pat. App. Publication No. 2017-0360397 A1 (and assigned to the assignee of the instant application), which is incorporated by reference herein in its entirety.

FIG. 20 should be understood to be non-limiting. For example, the ultrasound system 2000 may include fewer or more components than shown and the processing device 2002 may include fewer or more components than shown. In some embodiments, the processing device 2004 may be part of the ultrasound device 2002.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An apparatus, comprising:
a processing device comprising a processor and a display screen configured to display a graphical user interface (GUI), the processing device being in operative communication with an ultrasound device, wherein
the processing device is configured to:
  display, during ultrasound imaging, an ultrasound image on the GUI on the display screen;
  determine, during the ultrasound imaging and using a statistical model, a location of a specific point on an anatomical region shown in the ultrasound image at which to display an indicator; and
  determine, during ultrasound imaging, whether or not the anatomical region shown in the ultrasound image displayed on the GUI on the display screen is clipped by a field of view of the ultrasound image,
wherein when determining whether or not the anatomical region shown in the ultrasound image is clipped by the field of view of the ultrasound image, the processor:

determines a modified field of view that is offset from edges of the field of view toward the center of the field of view;

determines a number of pixels of the anatomical region that are between the edges of the field view and edges of the modified field of view;

determines the anatomical region shown in the ultrasound image is clipped by the field of view of the ultrasound image when the number of pixels exceeds a threshold number of pixels; and determines the anatomical region shown in the ultrasound image is not clipped by the field of view of the ultrasound image when the number of pixels does not exceed a threshold number of pixels;

wherein, in response to determining that the anatomical region shown in the ultrasound image is clipped by the field of view of the ultrasound image, the processing device is further configured to display, via the GUI, the indicator with a first aspect at the determined location and superimposed on the ultrasound image; and wherein, in response to determining that the anatomical region shown in the ultrasound image is not clipped by the field of view of the ultrasound image, the processing device is further configured to display, via the GUI, the indicator with a second aspect at the determined location and superimposed on the ultrasound image.

2. The apparatus of claim 1, wherein
the statistical model is trained to automatically determine the location of the specific point on the anatomical region shown in the ultrasound image at which to display the indicator.

3. The apparatus of claim 1, wherein
the processing device is configured, when determining, during the ultrasound imaging, whether or not the anatomical region shown in the ultrasound image is clipped by the field of view of the ultrasound image, to determine that the anatomical region is clipped by the field of view of the ultrasound image in a time period between display of a previous ultrasound image and display of a subsequent ultrasound image.

4. The apparatus of claim 1, wherein
the processing device is configured to display a measurement of a volume of the anatomical region.

5. The apparatus of claim 1, wherein
the specific point has predetermined mathematical characteristics.

6. The apparatus of claim 1, wherein
the processing device is configured to display the indicator in a time period between display of a previous ultrasound image and display of a subsequent ultrasound image.

7. The apparatus of claim 1, wherein
the anatomical region comprises a bladder.

8. The apparatus of claim 3, wherein
consecutive ultrasound images are displayed with a frame rate between 15-30 frames/second.

9. The apparatus of claim 4, wherein
the processing device is configured to display a second indicator indicating whether the measurement of the volume of the anatomical region is accurate.

10. The apparatus of claim 9, wherein
the second indicator comprises a symbol or text.

11. The apparatus of claim 5, wherein
the specific point includes a centroid of the anatomical region.

12. The apparatus of claim 6, wherein
consecutive ultrasound images are displayed with a frame rate between 15-30 frames/second.

13. An apparatus, comprising:
a processing device comprising a processor and a display screen configured to display a graphical user interface (GUI), the processing device being in operative communication with an ultrasound device, wherein
the processing device is configured to:
   display, during a three-dimensional ultrasound imaging sweep, at least one ultrasound image;
   determine, during the three-dimensional ultrasound imaging sweep and using a statistical model, a location of a specific point on an anatomical region shown in the at least one ultrasound image at which to display an indicator; and
   determine whether or not the anatomical region shown in the at least one ultrasound image is clipped by a field of view of the at least one ultrasound image collected during the three-dimensional ultrasound imaging sweep,
wherein when determining whether or not the anatomical region shown in the at least one ultrasound image is clipped by the field of view of the at least one ultrasound image collected during the three-dimensional ultrasound imaging sweep, the processor:
   determines a modified field of view that is offset from edges of the field of view toward the center of the field of view;
   determines a number of pixels of the anatomical region that are between the edges of the field of view and edges of the modified field of view;
   determines the anatomical region shown in the at least one ultrasound image is clipped by the field of view of the at least one ultrasound image collected during the three-dimensional ultrasound imaging sweep when the number of pixels exceeds a threshold number of pixels; and
   determines the anatomical region shown in the at least one ultrasound image is not clipped by the field of view of the at least one ultrasound image collected during the three-dimensional ultrasound imaging sweep when the number of pixels does not exceed a threshold number of pixels;
wherein, in response to determining that the anatomical region shown in the at least one ultrasound image is clipped by the field of view of the at least one ultrasound image collected during the three-dimensional ultrasound imaging sweep, the processing device is further configured to display, via the GUI, the indicator with a first aspect at the determined location and superimposed on the at least one ultrasound image; and
wherein, in response to determining that the anatomical region shown in the at least one ultrasound image is not clipped by the field of view of the at least one ultrasound image collected during the three-dimensional ultrasound imaging sweep, the processing device is further configured to display, via the GUI, the indicator with a second aspect at the determined location and superimposed on the at least one ultrasound image.

14. The apparatus of claim 13, wherein
the three-dimensional ultrasound imaging sweep comprises an elevational sweep.

15. The apparatus of claim 13, wherein
the processing device is configured to display a second indicator indicating that the anatomical region is clipped by the field of view of the at least one ultrasound image collected during the three-dimensional ultrasound imaging sweep.

16. The apparatus of claim 13, wherein the processing device is further configured to display a measurement of a volume of the anatomical region.

17. The apparatus of claim 15, wherein the indicator comprises text.

18. The apparatus of claim 16, wherein the anatomical region comprises a bladder.

* * * * *